(12) United States Patent
Wang et al.

(10) Patent No.: US 10,633,393 B2
(45) Date of Patent: *Apr. 28, 2020

(54) HETEROCYCLIC COMPOUNDS AS KINASE INHIBITORS

(71) Applicant: TRANSLATIONAL DRUG DEVELOPMENT, LLC, Scottsdale, AZ (US)

(72) Inventors: Tong Wang, Scottsdale, AZ (US); Stephen Gately, Scottsdale, AZ (US)

(73) Assignee: Translational Drug Development, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/551,694

(22) Filed: Aug. 26, 2019

(65) Prior Publication Data

US 2020/0017520 A1  Jan. 16, 2020

Related U.S. Application Data

(63) Continuation of application No. 15/574,800, filed as application No. PCT/US2016/033111 on May 18, 2016, now Pat. No. 10,392,402.

(60) Provisional application No. 62/203,070, filed on Aug. 10, 2015, provisional application No. 62/163,369, filed on May 18, 2015.

(51) Int. Cl.
*C07D 495/04* (2006.01)
*A61K 31/381* (2006.01)
*C07D 403/04* (2006.01)
*C07D 401/04* (2006.01)
*A61P 37/00* (2006.01)
*A61P 29/00* (2006.01)
*A61P 25/00* (2006.01)
*A61P 9/00* (2006.01)
*A61P 35/00* (2006.01)

(52) U.S. Cl.
CPC .............. *C07D 495/04* (2013.01); *A61P 9/00* (2018.01); *A61P 25/00* (2018.01); *A61P 29/00* (2018.01); *A61P 35/00* (2018.01); *A61P 37/00* (2018.01); *C07D 401/04* (2013.01); *C07D 403/04* (2013.01)

(58) Field of Classification Search
CPC ............................. C07D 495/04; A61K 31/381
See application file for complete search history.

(56) References Cited

U.S. PATENT DOCUMENTS 10,392,402 B2 * 8/2019 Wang ................. A61K 31/4184

* cited by examiner

*Primary Examiner* — Karen Cheng
(74) *Attorney, Agent, or Firm* — Rodney J. Fuller; Booth Udall Fuller, PLC

(57) ABSTRACT

The present invention is directed to certain amides and heterocyclic compounds. The present invention also relates to uses of these compounds to treat several diseases including autoimmune disorders, cardiovascular disorders, inflammation, central nervous system disorders, arterial thrombotic disorders, fibrotic disorders, glaucoma, and neoplastic disorders.

24 Claims, No Drawings

HETEROCYCLIC COMPOUNDS AS KINASE INHIBITORS

CROSS REFERENCE TO RELATED APPLICATIONS

This application is a continuation of U.S. patent application Ser. No. 15/574,800, filed Nov. 16, 2017 (published as US20180141959), which is the U.S. National Stage of International Application No. PCT/US2016/033111, filed May 18, 2016, which claims priority to U.S. Provisional Patent Application No. 62/203,070, filed Aug. 10, 2015, and U.S. Provisional Patent Application No. 62/163,369, filed May 18, 2015, the contents of each of which are incorporated herein by reference in their entireties.

FIELD OF THE INVENTION

The present invention relates to heterocyclic compounds, their compositions and medicaments containing the same, as well as processes for the preparation and use of such compounds, compositions and medicaments. Such compounds are potentially useful in the treatment of diseases associated with inappropriate tyrosine and/or serine/threonine kinase activity.

BACKGROUND OF THE INVENTION

An important large family of enzymes is the protein kinase enzyme family. Currently, there are about 500 different known protein kinases. Protein kinases serve to catalyze the phosphorylation of an amino acid side chain in various proteins by the transfer of the γ-phosphate of the ATP-Mg$^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied family of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK), includes cyclic AMP- and cyclic GMP-dependent protein kinases, calcium- and phospholipid-dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also under progress to identify modulators of tyrosine kinases as well.

A major signal transduction systems utilized by cells is the RhoA-signaling pathways. RhoA is a small GTP binding protein that can be activated by several extracellular stimuli such as growth factor, hormones, mechanic stress, osmotic change as well as high concentration of metabolite like glucose. RhoA activation involves GTP binding, conformation alteration, post-translational modification (geranylgeranyllization and farnesylation) and activation of its intrinsic GTPase activity. Activated RhoA is capable of interacting with several effector proteins including ROCKs and transmit signals into cellular cytoplasm and nucleus.

ROCK1 and 2 constitute a family of kinases that can be activated by RhoA-GTP complex via physical association. Activated ROCKs phosphorylate a number of substrates and play important roles in pivotal cellular functions. The substrates for ROCKs include myosin binding subunit of myosin light chain phosphatase (MBS, also named MYPT1), adducin, moesin, myosin light chain (MLC), LIM kinase as well as transcription factor FHL. The phosphorylation of theses substrates modulate the biological activity of the proteins and thus provide a means to alter cell's response to external stimuli. One well documented example is the participation of ROCK in smooth muscle contraction. Upon stimulation by phenylephrine, smooth muscle from blood vessels contracts. Studies have shown that phenylephrine stimulates alpha-adrenergic receptors and leads to the activation of RhoA. Activated RhoA in turn stimulates kinase activity of ROCK1 and which in turn phosphorylates MBS. Such phosphorylation inhibits the enzyme activity of myosin light chain phosphatase and increases the phosphorylation of myosin light chain itself by a calcium-dependent myosin light chain kinase (MLCK) and consequently increases the contractility of myosin-actin bundle, leading to smooth muscle contraction. This phenomena is also sometimes called calcium sensitization. In addition to smooth muscle contraction, ROCKs have also been shown to be involved in cellular functions including apoptosis, cell migration, transcriptional activation, fibrosis, cytokinesis, inflammation and cell proliferation. Moreover, in neurons ROCK plays a critical role in the inhibition of axonal growth by myelin-associated inhibitory factors such as i myelin-associated glycoprotein (MAG). ROCK-activity also mediates the collapse of growth cones in developing neurons. Both processes are thought to be mediated by ROCK-induced phosphorylation of substrates such as LIM kinase and myosin light chain phosphatase, resulting in increased contractility of the neuronal actin-myosin system. Inhibitors of ROCKs have been suggested for use in the treatments of a variety of diseases. They include cardiovascular diseases such as hypertension, chronic and congestive heart failure, cardiac hypertrophy, restenosis, chronic renal failure and atherosclerosis. In addition, because of its muscle relaxing properties, it is also suitable for asthma, male erectile dysfunctions, female sexual dysfunction and over-active bladder syndrome. ROCK inhibitors have been shown to possess anti-inflammatory properties. Thus they can be used as treatment for neuroinflammatory diseases such as stroke, multiple sclerosis, Alzheimer's disease, Parkinson's disease, amyotrophic lateral sclerosis and inflammatory pain, as well as other inflammatory diseases such as rheumatoid arthritis, irritable bowel syndrome, inflammatory bowel disease. In addition, based on their neurite outgrowth inducing effects, ROCK inhibitors could be useful drugs for neuronal regeneration, inducing new axonal growth and axonal rewiring across lesions within the CNS. ROCK inhibitors are therefore likely to be useful for regenerative (recovery) treatment of CNS disorders such as spinal cord injury, acute neuronal injury (stroke, traumatic brain injury), Parkinson's disease, Alzheimer's disease and other neurodegenerative disorders.

Since ROCK inhibitors reduce cell proliferation and cell migration, they could be useful in treating cancer and tumor metastasis. Furthermore, there is evidence suggesting that ROCK inhibitors suppress cytoskeletal rearrangement upon virus invasion, thus they also have potential therapeutic value in antiviral and anti-bacterial applications. ROCK inhibitors may also be useful for the treatment of insulin resistance and diabetes.

The inventors have discovered novel heterocyclic compounds, which are inhibitors of ROCK activity. Such derivatives are useful in the treatment of disorders associated with inappropriate ROCK activity.

SUMMARY OF THE INVENTION

The present invention is directed to a compound of Formula I:

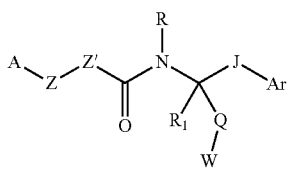

I or an enantiomer, a mixture of enantiomers, or a mixture of two or more diastereomers thereof; or a pharmaceutically acceptable salt, solvate, hydrate or physiologically functional derivative thereof;
wherein:
A is indazol-3-yl, pyrazol-4-yl,

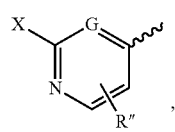

wherein (i) G is CR' or N; (ii) X is hydrogen, $C_{1-6}$ alkyl, $C_{3-7}$ cycloalkyl, —$OR_2$ or —$NR_3R_4$; and (iii) R', R", $R_2$, $R_3$ and $R_4$ are independently —H or $C_{1-6}$ alkyl or, $C_{3-7}$ cycloalkyl; Z is selected from the group consisting of:

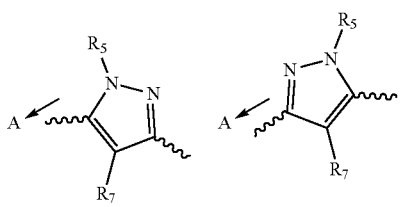

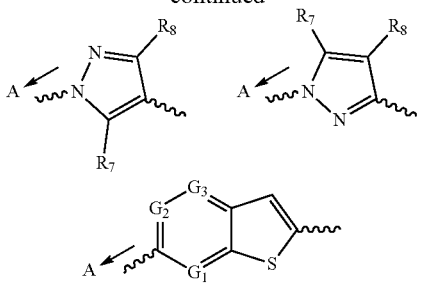

wherein (i) $R_5$ is —H, $C_{1-6}$ alkyl or $C_{3-7}$ cycloalkyl; (ii) $R_7$ and $R_8$ are independently —H, halo, $C_{1-6}$ alkyl, $C_{3-7}$ cycloalkyl, —O—($C_{1-6}$ alkyl), —OH, —CN, —COOR', —OC(O)R', NHR', N(R')$_2$, —NHC(O)R', —NHS(O)$_2$R', —C(O)NHR', or —S(O)$_2$R' wherein R' is —H, $C_{1-6}$ alkyl, or $C_{3-7}$ cycloalkyl; (iii) $G_1$, $G_2$ and $G_3$ are independently CH or N.

Z' is a bond, O or $NR_6$, wherein $R_6$ is —H, $C_{1-6}$ alkyl or $C_{3-7}$ cycloalkyl;
R is —H, $C_{1-6}$ alkyl or $C_{3-7}$ cycloalkyl;
$R_1$ is —H or $C_{1-6}$ alkyl;
Q is a bond or $C_{1-6}$ alkyl;
J is a bond or $C_{1-6}$ alkyl;
W is —H, —$OR_9$, —$NR_{10}R_{11}$, or —$S(O)_mR_{12}$, wherein (i) $R_9$, $R_{10}$ and $R_{11}$ are independently —H, $C_{1-6}$ alkyl, $C_{3-7}$ cycloalkyl, formyl, $C_{1-6}$ alkylcarbonyl, $C_{3-7}$ cycloalkylcarbonyl, or $C_{1-6}$ alkylsulfonyl; (ii) m is an integer from 0 to 2; and (iii) $R_{12}$ is $C_{1-6}$ alkyl or $C_{3-7}$ cycloalkyl; and Ar is a phenyl, naphthyl, or $C_{5-10}$ heterocycle, each of which is optionally substituted with halo, —OH, —CN, —$COOR_a$, —$OR_a$, —$SR_a$, —$OC(O)R_a$, —$NHR_a$, —$NR_aR_b$, —$NHC(O)R_a$, —$NHC(O)NR_aR_b$, —$C(O)NR_aR_b$, —$NS(O)_2R_a$, —$S(O)_2NR_aR_b$, —$S(O)_2R_a$, guanidino, nitro, nitroso, $C_{1-6}$ alkyl, aryl, $C_{3-7}$ cycloalkyl, or 3- to 10-membered heterocycle, wherein the $C_{1-6}$ alkyl, aryl, $C_{3-7}$ cycloalkyl, or 3 to 10-membered heterocycle is unsubstituted or substituted with one or more of halo, —OH, —CN, —$COOR_a$, —$OR_a$, —$SR_a$, —$OC(O)R_a$, —$NHR_a$, —$NR_aR_b$, —$NHC(O)R_a$, —$NHC(O)NR_aR_b$, —$C(O)NR_aR_b$, —$NS(O)_2R_a$, —$S(O)_2NR_aR_b$, —$S(O)_2R_a$, guanidino, nitro, nitroso, $C_{1-6}$ alkyl, aryl, or $C_{3-7}$ cycloalkyl; wherein each of $R_a$ and $R_b$ is independently H or $C_{1-6}$ alkyl; and optionally $R_a$ and $R_b$ together attaching to N or O form a 4- to 8-membered heterocycle.

In one embodiment, the present invention is directed to a compound of Formula II:

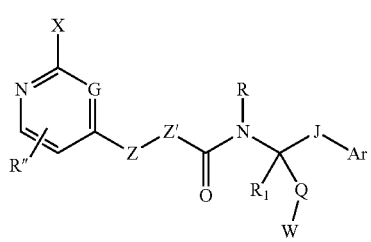

II wherein (i) G is CR' or N; (ii) X is hydrogen, $C_{1-6}$ alkyl, $C_{3-7}$ cycloalkyl, —$OR_2$ or —$NR_3R_4$; and (iii) R', R", $R_2$, $R_3$ and $R_4$ are independently —H or $C_{1-6}$ alkyl or, $C_{3-7}$ cycloalkyl; Z is selected from the group consisting of:

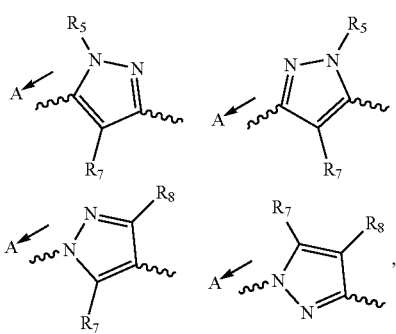

wherein (i) $R_5$ is —H, $C_{1-6}$ alkyl or $C_{3-7}$ cycloalkyl; (ii) $R_7$ and $R_8$ are independently —H, halo, $C_{1-6}$ alkyl, $C_{3-7}$ cycloalkyl, —O—($C_{1-6}$ alkyl), —OH, —CN, —COOR', —OC(O)R', NHR', N(R')$_2$, —NHC(O)R', —NHS(O)$_2$R', —C(O)NHR', or —S(O)$_2$R' wherein R' is —H, $C_{1-6}$ alkyl, or $C_{3-7}$ cycloalkyl; (iii) $G_2$, $G_3$ and $G_4$ are independently CH or N.

Z' is a bond, O or NR$_6$, wherein R$_6$ is —H, $C_{1-6}$ alkyl or $C_{3-7}$ cycloalkyl;

R is —H, $C_{1-6}$ alkyl or $C_{3-7}$ cycloalkyl;

$R_1$ is —H or $C_{1-6}$ alkyl;

Q is a bond or $C_{1-6}$ alkyl;

J is a bond or $C_{1-6}$ alkyl;

W is —H, —OR$_9$, —NR$_{10}$R$_{11}$, or —S(O)$_m$R$_{12}$, wherein (i) R$_9$, R$_{10}$ and R$_{11}$ are independently —H, $C_{1-6}$ alkyl, $C_{3-7}$ cycloalkyl, formyl, $C_{1-6}$ alkylcarbonyl, $C_{3-7}$ cycloalkylcarbonyl, or $C_{1-6}$ alkylsulfonyl; (ii) m is an integer from 0 to 2; and (iii) R$_{12}$ is $C_{1-6}$ alkyl or $C_{3-7}$ cycloalkyl; and Ar is a phenyl, naphthyl, or $C_{5-10}$ heterocycle, each of which is optionally substituted with halo, —OH, —CN, —COOR$_a$, —OR$_a$, —SR$_a$, —OC(O)R$_a$, —NHR$_a$, —NR$_a$R$_b$, —NHC(O)R$_a$, —NHC(O)NR$_a$R$_b$, —C(O)NR$_a$R$_b$, —NS(O)$_2$R$_a$, —S(O)$_2$NR$_a$R$_b$, —S(O)$_2$R$_a$, guanidino, nitro, nitroso, $C_{1-6}$ alkyl, aryl, $C_{3-7}$ cycloalkyl, or 3- to 10-membered heterocycle, wherein the $C_{1-6}$ alkyl, aryl, $C_{3-7}$ cycloalkyl, or 3 to 10-membered heterocycle is unsubstituted or substituted with one or more of halo, —OH, —CN, —COOR$_a$, —OR$_a$, —SR$_a$, —OC(O)R$_a$, —NHR$_a$, —NR$_a$R$_b$, —NHC(O)R$_a$, —NHC(O)NR$_a$R$_b$, —C(O)NR$_a$R$_b$, —NS(O)$_2$R$_a$, —S(O)$_2$NR$_a$R$_b$, —S(O)$_2$R$_a$, guanidino, nitro, nitroso, $C_{1-6}$ alkyl, aryl, or $C_{3-7}$ cycloalkyl; wherein each of R$_a$ and R$_b$ is independently H or $C_{1-6}$ alkyl; and optionally R$_a$ and R$_b$ together attaching to N or O form a 4- to 8-membered heterocycle.

In another embodiment, the present invention is directed to a compound of Formula III:

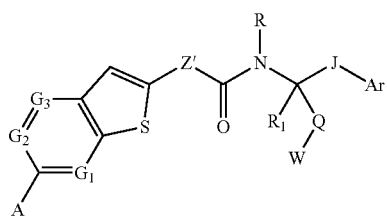

III

Wherein A is indazol-3-yl, pyrazol-4-yl,

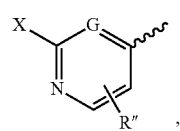

wherein (i) G is CR' or N; (ii) X is hydrogen, $C_{1-6}$ alkyl, $C_{3-7}$ cycloalkyl, —OR$_2$ or —NR$_3$R$_4$; and (iii) R', R", $R_2$, $R_3$ and $R_4$ are independently —H or $C_{1-6}$ alkyl or, $C_{3-7}$ cycloalkyl;

$G_5$, $G_6$ and $G_7$ are independently CH or N.

Z' is a bond, O or NR$_6$, wherein R$_6$ is —H, $C_{1-6}$ alkyl or $C_{3-7}$ cycloalkyl;

R is —H, $C_{1-6}$ alkyl or $C_{3-7}$ cycloalkyl;

$R_1$ is —H or $C_{1-6}$ alkyl;

Q is a bond or $C_{1-6}$ alkyl;

J is a bond or $C_{1-6}$ alkyl;

W is —H, —OR$_9$, —NR$_{10}$R$_{11}$, or —S(O)$_m$R$_{12}$, wherein (i) R$_9$, R$_{10}$ and R$_{11}$ are independently —H, $C_{1-6}$ alkyl, $C_{3-7}$ cycloalkyl, formyl, $C_{1-6}$ alkylcarbonyl, $C_{3-7}$ cycloalkylcarbonyl, or $C_{1-6}$ alkylsulfonyl; (ii) m is an integer from 0 to 2; and (iii) R$_{12}$ is $C_{1-6}$ alkyl or $C_{3-7}$ cycloalkyl; and Ar is a phenyl, naphthyl, or $C_{5-10}$ heterocycle, each of which is optionally substituted with halo, —OH, —CN, —COOR$_a$, —OR$_a$, —SR$_a$, —OC(O)R$_a$, —NHR$_a$, —NR$_a$R$_b$, —NHC(O)R$_a$, —NHC(O)NR$_a$R$_b$, —C(O)NR$_a$R$_b$, —NS(O)$_2$R$_a$, —S(O)$_2$NR$_a$R$_b$, —S(O)$_2$R$_a$, guanidino, nitro, nitroso, $C_{1-6}$ alkyl, aryl, $C_{3-7}$ cycloalkyl, or 3- to 10-membered heterocycle, wherein the $C_{1-6}$ alkyl, aryl, $C_{3-7}$ cycloalkyl, or 3 to 10-membered heterocycle is unsubstituted or substituted with one or more of halo, —OH, —CN, —COOR$_a$, —OR$_a$, —SR$_a$, —OC(O)R$_a$, —NHR$_a$, —NR$_a$R$_b$, —NHC(O)R$_a$, —NHC(O)NR$_a$R$_b$, —C(O)NR$_a$R$_b$, —NS(O)$_2$R$_a$, —S(O)$_2$NR$_a$R$_b$, —S(O)$_2$R$_a$, guanidino, nitro, nitroso, $C_{1-6}$ alkyl, aryl, or $C_{3-7}$ cycloalkyl; wherein each of R$_a$ and R$_b$ is independently H or $C_{1-6}$ alkyl; and optionally R$_a$ and R$_b$ together attaching to N or O form a 4- to 8-membered heterocycle.

In some embodiments, the present invention is directed to a compound of Formula I, II, and/or III selected from the group consisting of:

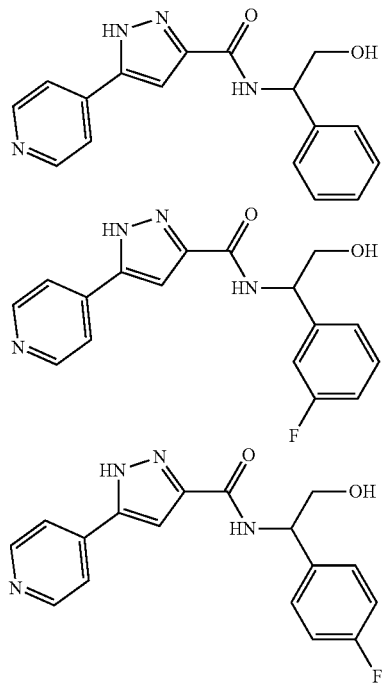

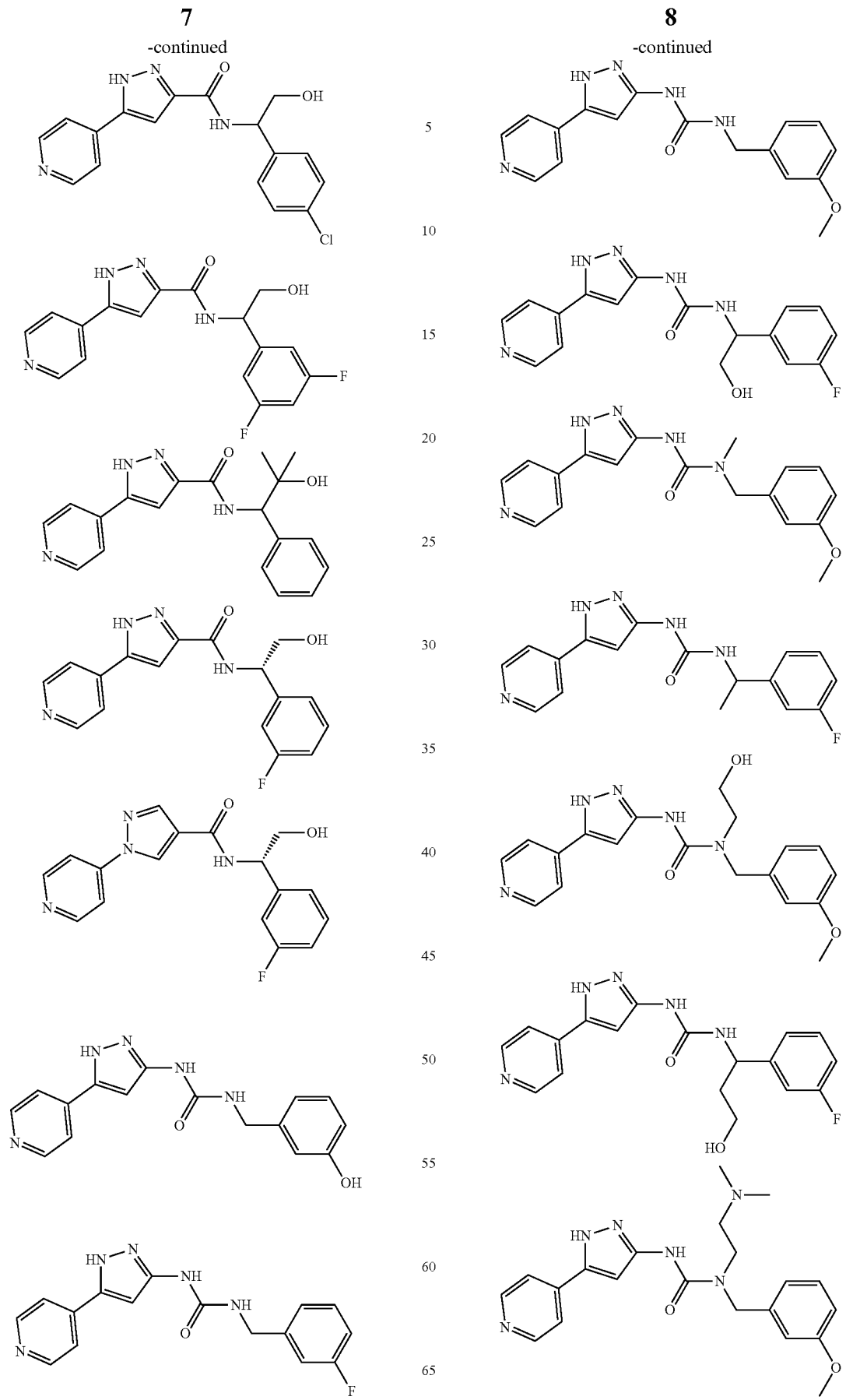

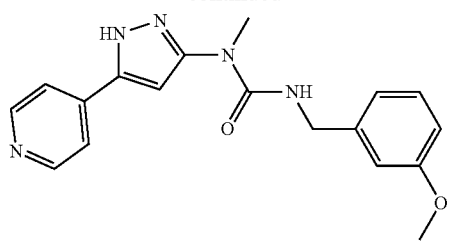
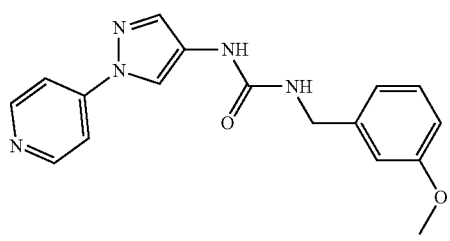
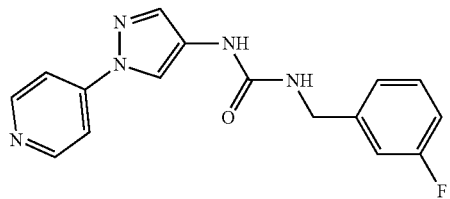
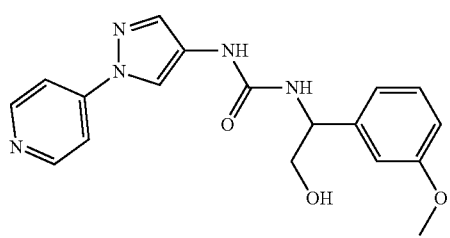
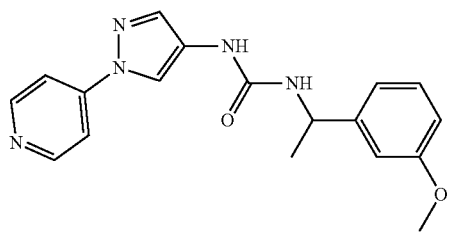
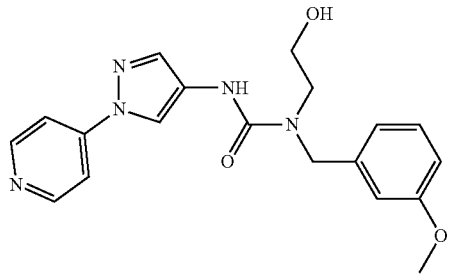
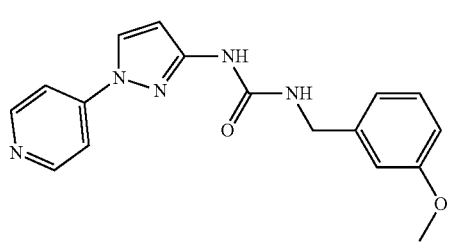
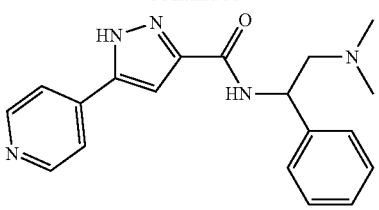
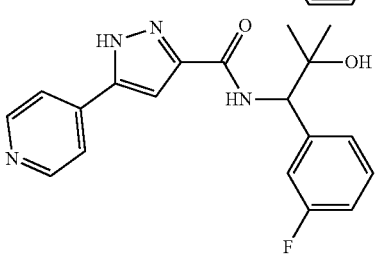
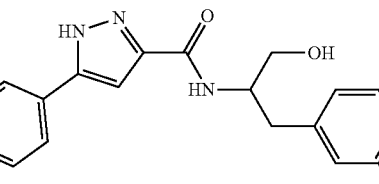
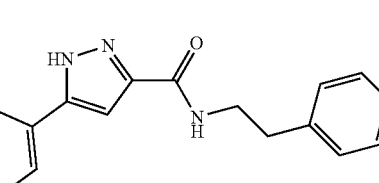
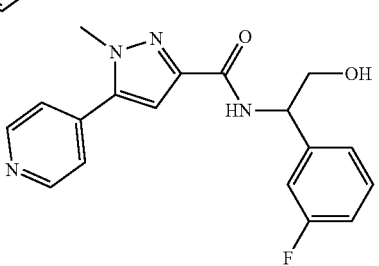
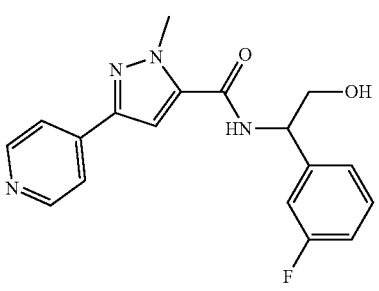
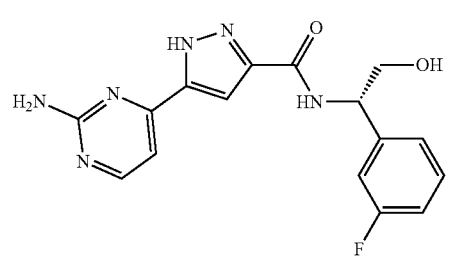

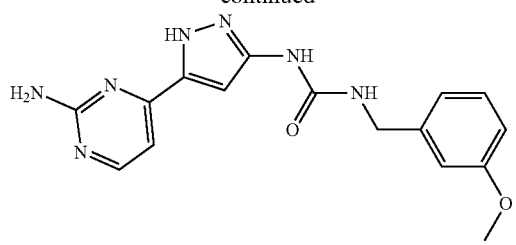
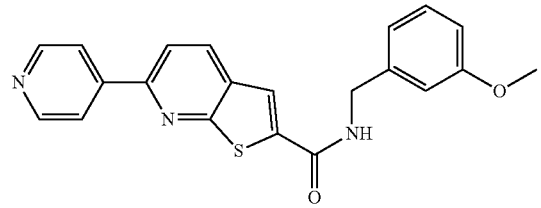
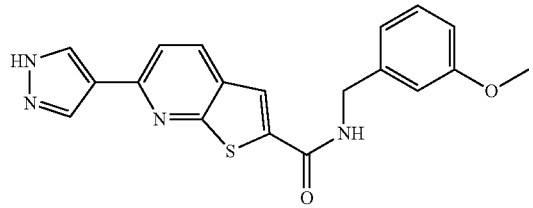
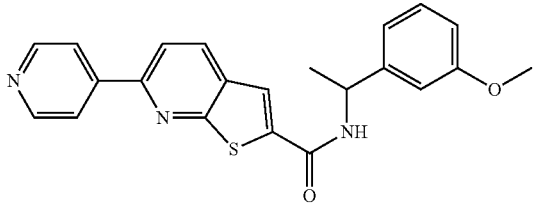
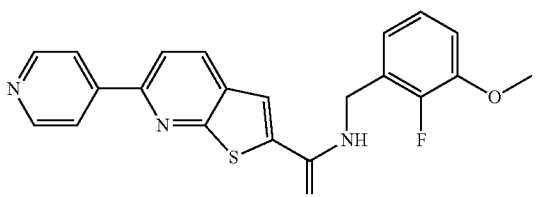
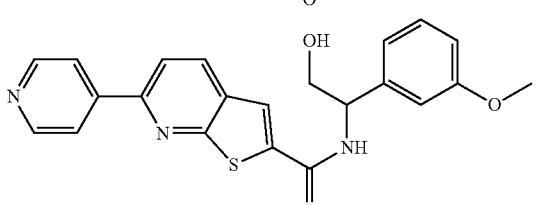
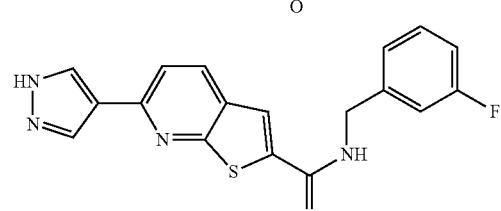
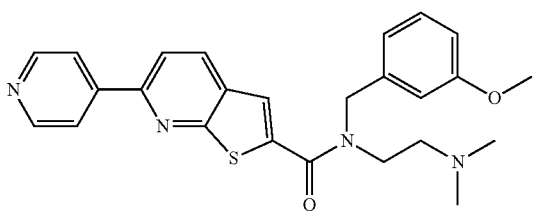
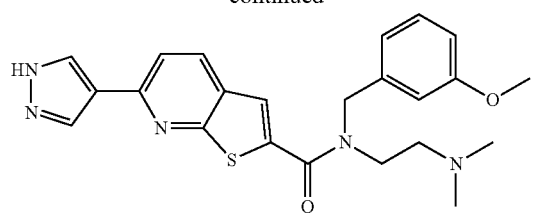
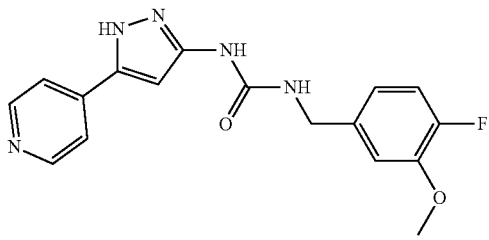
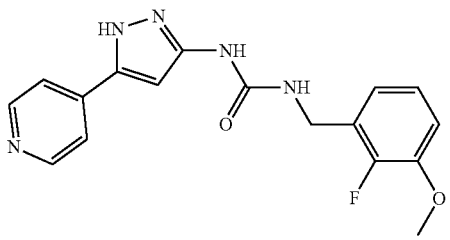
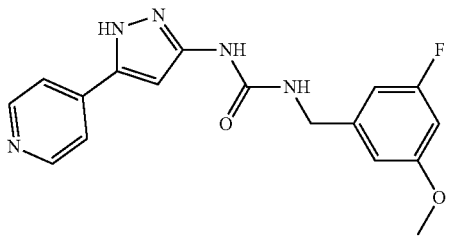
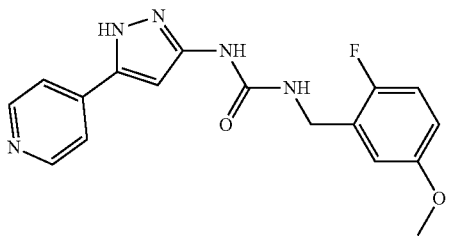
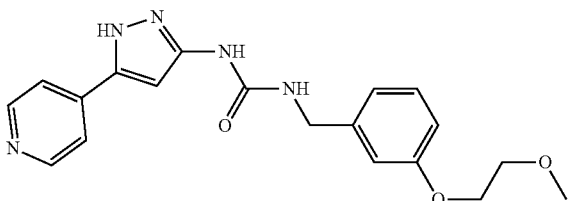
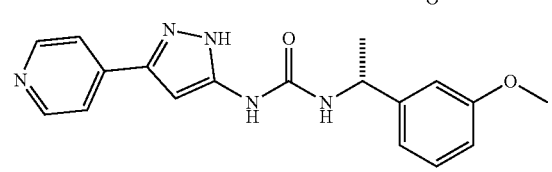
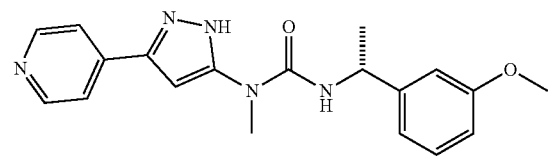

-continued

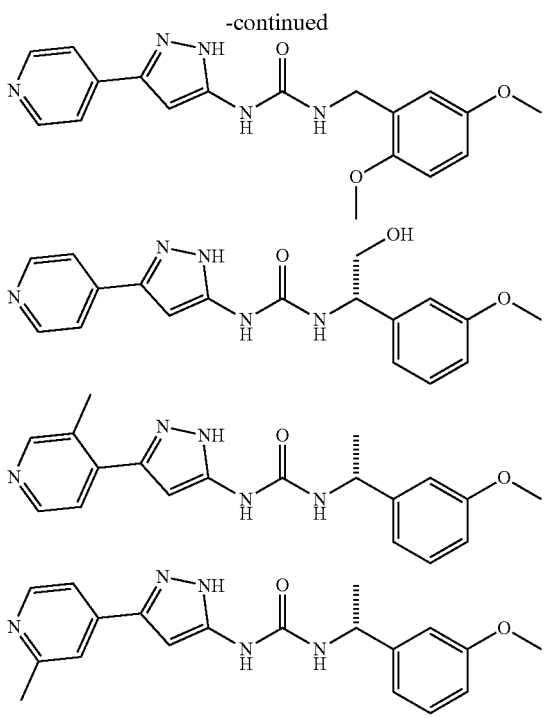

The present invention is also directed to a compound of Formula V:

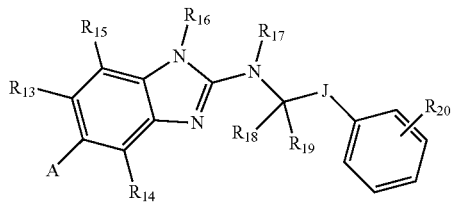

or an enantiomer, a mixture of enantiomers, or a mixture of two or more diastereomers thereof; or a pharmaceutically acceptable salt, solvate, hydrate or physiologically functional derivative thereof;
wherein:
A is indazol-3-yl, pyrazol-4-yl or

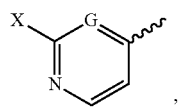

wherein (i) G is CH or N; and (ii) X is hydrogen, —OR$_2$ or —NR$_3$R$_4$, wherein each of R$_2$, R$_3$ and R$_4$ is independently —H or C$_{1-6}$ alkyl; each of R$_{13}$ and R$_{14}$ is independently —H, halo, C$_{1-6}$ alkyl, or C$_{3-7}$ cycloalkyl; each of R$_{15}$ and R$_{20}$ is independently —H, halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, C$_{1-6}$ alkyl, aryl, C$_{3-7}$ cycloalkyl, and 3- to 10-membered heterocycle, wherein each of the C$_{1-6}$ alkyl, aryl, C$_{3-7}$ cycloalkyl, or 3- to 10-membered heterocycle independently is unsubstituted or substituted with one or more of halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, C$_{1-6}$ alkyl, aryl, C$_{3-7}$ cycloalkyl; wherein each of R' and R" is independently —H or C$_{1-6}$ alkyl; and optionally R' and R" together attaching to N or O form a 4- to 8-membered heterocycle;
each of R$_{16}$, R$_{17}$, R$_8$ and R$_{19}$ is independently —H, C$_{1-6}$ alkyl, aryl, C$_{3-7}$ cycloalkyl, or 3 to 10-membered heterocycle; wherein the C$_{1-6}$ alkyl, aryl, C$_{3-7}$ cycloalkyl, or 3- to 10-membered heterocycle is unsubstituted or substituted with one or more of halo, —OH, —CN, —COOR$_a$, —OR$_a$, —SR$_a$, —OC(O)R$_a$, —NHR$_a$, —NR$_a$R$_b$, —NHC(O)R$_a$, —NHC(O)NR$_a$R$_b$, —C(O)NR$_a$R$_b$, —NS(O)$_2$R$_a$, —S(O)$_2$NR$_a$R$_b$, —S(O)$_2$R$_a$, guanidino, nitro, nitroso, C$_{1-6}$ alkyl, aryl, C$_{3-7}$ cycloalkyl; wherein each of R$_a$ and R$_b$ is independently —H or C$_{1-6}$ alkyl; and optionally R$_a$ and R$_b$ together attaching to N or O forms a 4- to 8-membered heterocycle; and
J is a bond or C$_{1-6}$ alkyl.

In certain aspects, A is pyrazol-4-yl. In other aspects, A is pyridine-4-yl. In one aspect, the present invention relates to a compound of Formula II wherein both R$_{13}$ and R$_{14}$ are methyl.

In some embodiments, the present invention is directed to a compound of Formula V is selected from the group consisting of:

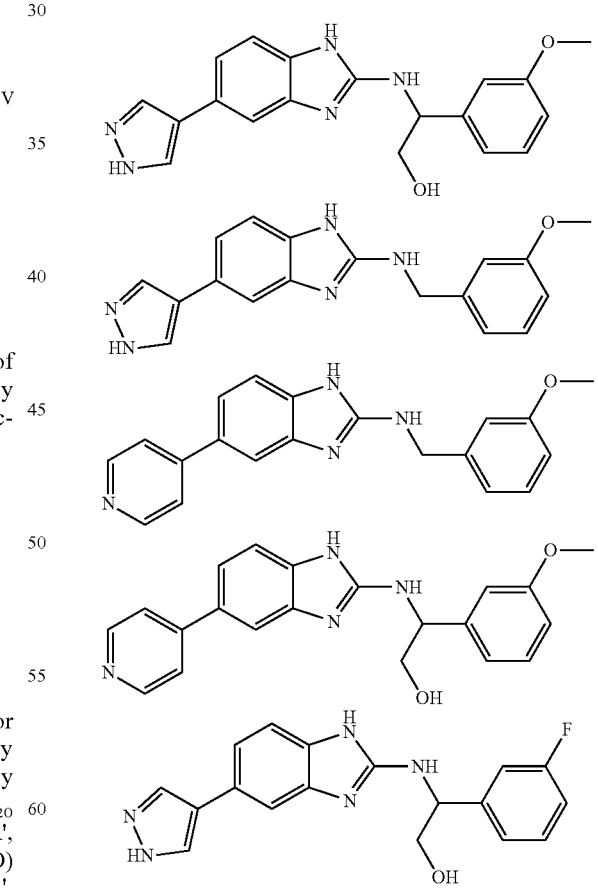

In certain aspects, the present invention provides a compound as disclosed herein for use in treating a disease related to upregulation of Rho kinase-signaling pathways.

In other aspects, the present invention is directed to a method of treating an autoimmune disorder in a subject comprising: administering to the subject a therapeutically effective amount of a compound disclosed herein. In one aspect, the autoimmune disorder is rheumatoid arthritis, multiple sclerosis, systemic lupus erythematosus (SLE), psoriasis, Crohn's disease, atopic dermatitis, eczema, or graft-versus-host disease (GVHD).

In some embodiments, the present invention provides a method of treating a cardiovascular disorder in a subject comprising: administering to the subject a therapeutically effective amount of a compound disclosed herein. In one embodiment, the cardiovascular disorder is hypertension, atherosclerosis, restenosis, cardiac hypertrophy, ocular hypertension, cerebral ischemia, cerebral vasospasm, or erectile dysfunction.

In other embodiments, the present invention provides a method of treating inflammation in a subject comprising: administering to the subject a therapeutically effective amount of a compound disclosed herein. In certain aspects, the inflammation is asthma, cardiovascular inflammation, renal inflammation or arteriosclerosis.

In certain aspects, the present invention provides a method of treating a central nervous system disorder in a subject comprising: administering to the subject a therapeutically effective amount of a compound disclosed herein. In one aspect, the central nervous system disorder is neuronal degeneration or spinal cord injury. In another aspect, the central nervous system disorder is Huntington's disease, Parkinson's Disease, Alzheimer's, Amyotrophic lateral sclerosis (ALS), or multiple sclerosis.

The present invention also provides a method of treating an arterial thrombotic disorder in a subject comprising: administering to the subject a therapeutically effective amount of a compound disclosed herein. In one embodiment, the arterial thrombotic disorder is platelet aggregation, or leukocyte aggregation.

In other aspects, the present invention relates to a method of treating a fibrotic disorder in a subject comprising: administering to the subject a therapeutically effective amount of a compound disclosed herein. In one embodiment, the fibrotic disorder is liver fibrosis, lung fibrosis, or kidney fibrosis.

The present invention also relates to a method of treating glaucoma or regulating intraocular pressure in a subject comprising administering to the subject a therapeutically effective amount of a compound disclosed herein. In one aspect, the glaucoma is primary open-angle glaucoma, acute angle-closure glaucoma, pigmentary glaucoma, congenital glaucoma, normal tension glaucoma, or secondary glaucoma.

In some embodiments, the present invention is directed to a method of treating a neoplastic disease in a subject comprising: administering to the subject a therapeutically effective amount of a compound disclosed herein. In certain aspects, the neoplastic disorder is a lymphoma, carcinoma, leukemia, sarcoma, or blastoma. In other aspects, the neoplastic disorder is squamous cell cancer, small-cell king cancer, pituitary cancer, esophageal cancer, astrocytoma, soft tissue sarcoma, non-small cell lung cancer, adenocarcinoma of the king, squamous carcinoma of the king, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, or head and neck cancer.

In yet other embodiments, the present invention provides a method of treating metabolic syndrome, insulin resistance, hyperinsulinemia, type 2 diabetes, or glucose intolerance in a subject comprising administering to the subject a therapeutically effective amount of a compound disclosed herein.

In one embodiment, the present invention relates to a method of treating osteoporosis or promoting bone formation in a subject comprising administering to the subject a therapeutically effective amount of a compound disclosed herein.

In another embodiment, the present invention relates to a method of treating an ocular disorder having an angiogenic component comprising administering to the subject a therapeutically effective amount of a compound disclosed herein and an angiogenesis inhibitor. In certain aspects, the ocular disorder is age related macular degeneration (AMD), choroidal neovascularization (CNV), diabetic macular edema (DME), iris neovascularization, uveitis, neo vascular glaucoma, or retinitis of prematurity (ROP).

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

It will be understood that "substituted", "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described herein below.

The term "alkyl," as used herein unless otherwise defined, refers to a straight or branched saturated group derived from the removal of a hydrogen atom from an alkane. Representative straight chain alkyl groups include -methyl, -ethyl, -n-propyl, -n-butyl, -n-pentyl, and n-heptyl. Representative branched alkyl groups include -isopropyl, -sec-butyl, -isobutyl, -tert-butyl, -isopentyl, -neopentyl, 1-methylbutyl, 2-methylbutyl, 3-methylbutyl, 1,1-dimethylpropyl and 1,2-dimethylpropyl.

As used herein, halo groups include any halogen. Examples include but are not limited to —F, —Cl, —Br, or —I.

A $C_1$-$C_6$ alkyl group includes any straight or branched, saturated or unsaturated, substituted or unsubstituted hydrocarbon comprised of between one and six carbon atoms. Examples of —$C_1$-$C_6$ alkyl groups include, but are not limited to methyl, ethyl, propyl, isopropyl, butyl, sec-butyl, tert-butyl, pentyl, isopentyl, neopentyl, hexyl, isohexyl, neohexyl, ethylenyl, propylenyl, 1-butenyl, 2-butenyl, 1-pentenyl, 2-pentenyl, 1-hexenyl, 2-hexenyl, 3-hexenyl, acetylenyl, pentynyl, 1-butynyl, 2-butynyl, 1-pentynyl, 2-pentynyl, 1-hexynyl, 2-hexynyl and 3-hexynyl groups. Substituted —$C_1$-$C_6$ alkyl groups may include any applicable chemical moieties. Examples of groups that may be substituted onto any of the above listed —$C_1$-$C_6$ alkyl groups include but are not limited to the following examples: halo, —$C_1$-$C_6$ alkyl, —O—($C_1$-$C_6$ alkyl), $C_3$-$C_7$ cycloalkyl, —OH, —CN, —COOR', —OC(O)R', —NHR', N(R')$_2$, —NHC(O)R' or —C(O)NHR' groups. The groups denoted R' above may be —H, any —$C_1$-$C_6$ alkyl, or two R' may, optionally with a nitrogen or an oxygen atom which they are bound to, form a 3-, 4-, 5-, 6-, 7-membered ring system when the substitution is —N(R')$_2$;

An aryl group includes any unsubstituted or substituted phenyl or napthyl group. Examples of groups that may be substituted onto any aryl group include, but are not limited to: halo, —$C_1$-$C_6$ alkyl, —O—($C_1$-$C_6$ alkyl), —OH, —CN, —COOR', —OC(O)R', NHR', N(R') 2, —NHC(O), R', or —C(O)NEtR'. The group denoted R' may be —H or any —$C_1$-$C_6$ alkyl.

A $C_3$-$C_7$ cycloalkyl group includes any 3-, 4-, 5-, 6-, or 7-membered substituted or unsubstituted non-aromatic carbocyclic ring. Examples of $C_3$-$C_7$ cycloalkyl groups include, but are not limited to, cyclopropyl, cyclobutyl, cyclopentyl, cyclopentadienyl, cyclohexyl, cyclohexenyl, cycloheptyl, cycloheptanyl, 1,3-cyclohexadienyl,-1, 4-cyclohexadienyl,-1, 3-cycloheptadienyl, and-1,3,5-cycloheptatrienyl groups. Examples of groups that may be substituted onto $C_3$-$C_7$ cycloalkyl groups include, but are not limited to: -halo, —$C_1$-$C_6$ alkyl, —O—($C_1$-$C_6$ alkyl), —OH, —CN, —COOR', —OC(O) R', NHR', N(R')2, —NHC(O)R' or —C(O)NHR' groups. The groups denoted R' above include an —H or any unsubstituted —$C_1$-$C_6$ alkyl, examples of which are listed above. Halo groups include any halogen. Examples include but are not limited to —F, —Cl, —Br, or —I.

A heterocycle may be any optionally substituted saturated, unsaturated or aromatic cyclic moiety wherein said cyclic moiety is interrupted by at least one heteroatom selected from oxygen (O), sulfur (S) or nitrogen (N). Heterocycles may be monocyclic or polycyclic rings. For example, suitable substituents include halogen, halogenated C1-6 alkyl, halogenated C1-6 alkoxy, amino, amidino, amido, azido, cyano, guanidino, hydroxyl, nitro, nitroso, urea, OS(O)$_2$R; OS(O)$_2$OR, S(O)$_2$OR S(O)$_{0-2}$R, C(O)OR wherein R may be H, $C_1$-$C_6$ alkyl, aryl or 3 to 10 membered heterocycle) OP(O)OR$_1$OR$_2$, P(O)OR$_1$OR$_2$, SO$_2$NR$_1$R$_2$, NR$_1$SO$_2$R$_2$ C(R$_1$)NR$_2$ C(R$_1$)NOR$_2$, R1 and R2 may be independently H, $C_1$-$C_6$ alkyl, aryl or 3 to 10 membered heterocycle), NR$_1$C(O)R$_2$, NR$_1$C(O)OR$_2$, NR$_3$C(O)NR$_2$R$_1$, C(O)NR$_1$R$_2$, OC(O)NR$_1$R$_2$. For these groups, R$_1$, R$_2$ and R$_3$ are each independently selected from H, $C_1$-$C_6$ alkyl, aryl or 3 to 10 membered heterocycle or R$_1$ and R$_2$ are taken together with the atoms to which they are attached to form a 3 to 10 membered heterocycle.

Possible substituents of heterocycle groups include halogen (Br, Cl, I or F), cyano, nitro, oxo, amino, C1-4 alkyl (e.g., $CH_3$, $C_2H_5$, isopropyl) $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl —S— (e.g., $CH_3S$, $C_2H_5S$), halogenated $C_{1-4}$ alkyl —S— (e.g., $CF_3S$, $C_2F_5S$), benzyloxy, and pyrazolyl.

Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl groups.

The invention further encompasses any other physiochemical or sterochemical form that the compound may assume. Such forms include diastereomers, racemates, isolated enantiomers, hydrated forms, solvated forms, any known or yet to be disclosed crystalline or amorphous form including all polymorphic crystalline forms. Amorphous forms lack a distinguishable crystal lattice and therefore lack an orderly arrangement of structural units. Many pharmaceutical compounds have amorphous forms. Methods of generating such chemical forms will be well known by one with skill in the art.

Another aspect of the invention is that the carbon atom bearing R$_1$ and -QW in Formula I and may have "S" or "R" configuration. All diastereomers, racemates, and isolated enantiomers are within the scope of the invention.

Racemates, individual enantiomers, or diasteromers of the compound may be prepared by specific synthesis or resolution through any method now known or yet to be disclosed. For example, the compound may be resolved into it enantiomers by the formation of diasteromeric pairs through salt formation using an optically active acid. Enantiomers are fractionally crystallized and the free base regenerated. In another example, enantiomers may be separated by chromatography. Such chromatography may be any appropriate method now known or yet to be disclosed that is appropriate to separate enantiomers such as HPLC on a chiral column.

The benzamide and pyrazole moiety and its intermediates may exist in different tautomeric forms. Tautomers include any structural isomers of different energies that have a low energy barrier to interconversion. One example is proton tautomers (prototropic tautomers.) In this example, the interconversions occur via the migration of a proton. Examples of prototropic tautomers include, but are not limited to keto-enol and imine-enamine isomerizations. In another example illustrated graphically below, proton migration between the 1-position, 2-amino and 3-position nitrogen atoms of a 2-aminobenzimidazole ring may occur. As a result, Formulas IIa, IIb and IIc are tautomeric forms of each other:

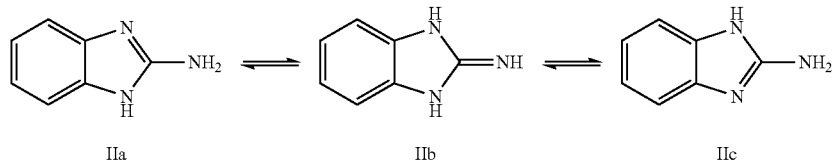 [SMILES: Nc1nc2ccccc2[nH]1 ; N=c1[nH]c2ccccc2[nH]1 ; Nc1nc2ccccc2[nH]1]

Similarly, Formulas IIIa and IIIb are tautomeric forms of each other:

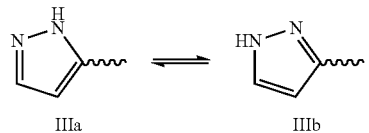

In some aspects of the invention the compound is in the form of a pharmaceutically acceptable salt. Pharmaceutically acceptable salts include any salt derived from an organic or inorganic acid. Examples of such salts include but are not limited to the following: salts of hydrobromic acid, hydrochloric acid, nitric acid, phosphoric acid and sulphuric acid. Organic acid addition salts include, for example, salts of acetic acid, benzenesulphonic acid, benzoic acid, camphorsulphonic acid, citric acid, 2-(4-chlorophenoxy)-2-methylpropionic acid, 1, 2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl) benzoicacid, 1-hydroxy-2-naphthoicacid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulpuric acid, mucic acid, 2-naphthalenesulphonic acid, pamoic acid, pantothenic acid, phosphanilic acid ((4-aminophenyl) phosphonic acid), picric acid, salicylic acid, stearic acid, succinic acid, tannic acid, tartaric acid, terephthalic acid, p-toluenesulphonic acid, 10-undecenoic acid or any other such acid now known or yet to be disclosed. It will be appreciated that such salts, provided that they are pharmaceutically acceptable, may be used in therapy. Such salts may be prepared by reacting the compound with a suitable acid in a manner known by those skilled in the art.

In some embodiments, the compounds of the present invention cause kinase inhibition in vitro and/or in vivo. Methods of determining kinase inhibition are well known in the art. For example, kinase activity of an enzyme and the inhibitory capacity of a test compound can be determined by measuring enzyme specific phosphorylation of a substrate. Commercial assays and kits can be employed. For example, kinase inhibition can be determined using an IMAP® assay (Molecular Devices). This assay method involves the use of a fluorescently-tagged peptide substrate. Phosphorylation of the tagged peptide by a kinase of interest promotes binding of the peptide to a trivalent metal-based nanoparticle via the specific, high affinity interaction between the phospho-group and the trivalent metal. Proximity to the nanoparticle results in increased fluorescence polarization. Inhibition of the kinase by a kinase inhibitor prevents phosphorylation of the substrate and thereby limits binding of the fluorescently-tagged substrate to the nanoparticle. Such an assay can be compatible with a microwell assay format, allowing simultaneous determination of $IC_{50}$ of multiple compounds.

In another aspect of the present invention there is provided a method of treating a patient suffering from a disease comprising administering to a patient in need of such treatment a therapeutically effective amount of a compound of the present invention. The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment, e.g., reasonable side effects applicable to any medical treatment.

Compounds of the invention are useful for treatment of patients suffering from cardiovascular and non-cardiovascular diseases, such as hypertension, pulmonary hypertension, atherosclerosis, restenosis, coronary heart disease, cardiac hypertrophy, ocular hypertension, retinopathy, ischemic diseases, cerebral ischemia, cerebral vasospasm, penile erectile dysfunction, peripheral circulatory disorder, peripheral artery occlusive disease, glaucoma, (e.g., regulating intraocular pressure), fibroid lung, fibroid liver, fibroid kidney, chronic obstructive pulmonary disease (COPD), adult respiratory distress syndrome, central nervous system disorders such as neuronal degeneration and spinal cord injury. Further, the compounds of the invention can be used to treat arterial thrombotic disorders such as platelet aggregation and leukocyte aggregation, and bone resorption.

In an embodiment of the invention, compounds are used to treat cerebral cavernous malformation (CCM). CCMs are vascular lesions consisting of clusters of leaky, dilated capillaries and are associated with central nervous system (CNS) disorders, including seizures and stroke. The loss of vascular integrity is thought to involve activation of RhoA and activation of ROCK, leading to changes in cytoskeletal stability and increased vascular permeability. The compounds of the invention inhibit ROCK activation and restore vascular endothelial function.

The compounds of the invention can also be used to treat glaucoma. There are several types of glaucoma which can be treated, including, without limitation, the following types. The two most common, primary open-angle glaucoma and acute angle-closure glaucoma are characterized by high ocular pressure. Pigmentary glaucoma and congenital glaucoma also are characterized by reduced fluid outflow and high intraocular pressure (IOP). Normal tension glaucoma is thought to be due to another mechanism, in particular poor blood flow to the optic nerve. Secondary glaucoma can result from injury, infection, inflammation, tumor or cataracts, and is also associated with prolonged use of steroids, systemic hypertension, diabetic retinopathy, and central retinal vein occlusion.

In certain embodiments, the compounds of the invention are used to treat inflammation, including, but not limited to asthma, cardiovascular inflammation, renal inflammation, atherosclerosis and arteriosclerosis.

In some embodiments, the compounds of the invention inhibit tumor cell growth and metastasis, and angiogenesis, and are useful for treating neoplastic diseases. Neoplastic diseases include any malignant growth or tumor caused by abnormal or uncontrolled cell division, and may spread to other parts of the body through the lymphatic system or the blood stream Neoplastic disease includes, without limitation, lymphoma (a neoplasm of lymph tissue that is usually malignant), carcinoma (any malignant tumor derived from epithelial tissue), leukemia (malignant neoplasm of blood-forming tissues; characterized by abnormal proliferation of leukocytes), sarcoma (a usually malignant tumor arising from connective tissue (bone or muscle etc.), and blastoma (malignancy in precursor cells). Non-limiting examples include squamous cell cancer, small-cell lung cancer, pituitary cancer, esophageal cancer, astrocytoma, soft tissue sarcoma, non-small cell king cancer, adenocarcinoma of the lung, squamous carcinoma of the king, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

According to one aspect of the invention, the inventive compounds are used to effect weight loss and/or limit weight gain. In a preferred embodiment, the compound is ROCK2 selective. ROCK-2 inhibitors promote weight loss in normal subjects, and limit weight gain in subjects prone to obesity.

In an embodiment of the invention, the inventive compound is used to reduce or prevent insulin resistance or restore insulin sensitivity. Accordingly, in one embodiment, the compounds of the invention are used to promote or restore insulin-dependent glucose uptake. In another embodiment of the invention, a compound of the invention is used to promote or restore glucose tolerance. In another embodiment of the invention, a compound of the invention is used to treat metabolic syndrome. In another embodiment, a compound of the invention is used to reduce or prevent hyperinsulinemia. In an embodiment of the invention, an inventive compound is used to treat diabetes (particularly type 2 diabetes). Compounds of the invention may also be used to promote or restore insulin-mediated relaxation of vascular smooth muscle cells (VSMCs).

The invention provides methods and compounds for treating diseases and disorders with an angiogenic component. According to the invention, in certain embodiments, such diseases and disorders are treated by administering to a subject an effective amount of a rho kinase inhibitor. In certain embodiments, the inventive compound is a ROCK2 selective inhibitor. According to the invention, such diseases and disorders can also be treated by administering an effective amount of a rho kinase inhibitor that inhibits ROCK2, and may be ROCK2 selective, and an effective amount of an angiogenesis inhibitor. According to the invention, ocular diseases and disorders having an angiogenic component are treated in this manner. In one embodiment, the invention provides a method of treating age related macular degeneration (AMD), which occurs in "dry" and "wet" forms. The "wet" form of AMD causes vision loss due to abnormal blood vessel growth (neovascularization). Bleeding, leaking, and scarring from these retinal blood vessels eventually causes irreversible damage to the photoreceptors. The dry form results from atrophy of the retinal pigment epithelial layer, which causes vision loss through loss of photoreceptors (rods and cones) in the central part of the eye. In another embodiment, the invention provides a method of treating choroidal neovascularization (CNV). Choroidal neovascularization is a process in which new blood vessels grow in the choroid, through the Bruch membrane and invade the subretinal space, and is a symptom of, among other causes, age-related macular degeneration, myopia and ocular trauma. In another embodiment, the invention provides a method of treating diabetic macular edema (DME). In another embodiment, the invention provides a method of treating macular edema that is secondary to branch retinal vein occlusion (BRVO) or central retinal vein occlusion (CRVO). In other embodiments, the diseases to be treated include, without limitation, retinal neovascularization, infectious and non-infectious, corneal neovascularization infectious and non-infectious, iris neovascularization, uveitis, neovascular glaucoma, and retinitis of prematurity (ROP). The method of treatment can be prophylactic, such as to stave off corneal neovascularization after corneal transplant, or to modulate the wound healing process in trabeculectomy surgery. These diseases and disorders may be characterized as having an angiogenic component. According to the invention, such disorders are treated by administering an inventive compound and an angiogenesis inhibitor.

Accordingly, in one such embodiment, the disease or disorder is AMD, and a subject in need of treatment for AMD is administered an amount of an inventive compound to treat AMD. In another embodiment, the subject is administered an inventive compound and an angiogenesis inhibitor in amounts effective to treat AMD. In such embodiments, a ROCK2-selective inhibitor may be preferred. In some embodiments, the angiogenesis inhibitor is a VEGFR2 antagonist. In certain such embodiments, the VEGFR2 antagonist binds to VEGF. In other such embodiments, the VEGFR2 antagonist binds to VEGFR2. Such VEGFR2-binding inhibitors include agents that bind to the extracellular domain of VEGFR2, including but not limited to antibodies and VEGFR2-binding fragments thereof and agents that interact with the intracellular domain of VEGFR2 and block activation of VEGFR2-dependent signal transduction. VEGFR2 antagonists further include agents that interact with other cellular components to block VEGFR2-dependent signal transduction. In other embodiments of the invention, other ocular diseases and disorders having an angiogenic component, such as are indicated above, are similarly treated.

According to the invention, an inventive compound and an angiogenesis inhibitor are administered to a subject in amounts effective amount to treat or preventing a pathologic condition characterized by excessive angiogenesis. Such conditions, involving for example, vascularization and/or inflammation, include atherosclerosis, rheumatoid arthritis (RA), hemangiomas, angiofibromas, and psoriasis. Other non-limiting examples of angiogenic disease are retinopathy of prematurity (retrolental fibroplastic), corneal graft rejection, corneal neovascularization related to complications of refractive surgery, corneal neovascularization related to contact lens complications, corneal neovascularization related to pterygium and recurrent pterygium, corneal ulcer disease, and non-specific ocular surface disease, insulin-dependent diabetes mellitus, multiple sclerosis, myasthenia gravis, Crohn's disease, autoimmune nephritis, primary biliary cirrhosis, acute pancreatitis, allograph rejection, allergic inflammation, contact dermatitis and delayed hypersensitivity reactions, inflammatory bowel disease, septic shock, osteoporosis, osteoarthritis, cognition defects induced by neuronal inflammation, Osier-Weber syndrome, restenosis, and fungal, parasitic and viral infections, including cytomegalovirus infections.

The invention further encompasses pharmaceutical compositions that include the disclosed compound as an ingredient. Such pharmaceutical compositions may take any physical form necessary depending on a number of factors including the desired method of administration and the physicochemical and stereochemical form taken by the disclosed compound or pharmaceutically acceptable salts of the compound. Such physical forms include a solid, liquid, gas, sol, gel, aerosol, or any other physical form now known or yet to be disclosed. The concept of a pharmaceutical composition including the disclosed compound also encompasses the disclosed compound or a pharmaceutically acceptable salt thereof without any other additive. The physical form of the invention may affect the route of administration and one skilled in the art would know to choose a route of administration that takes into consideration both the physical form of the compound and the disorder to be treated. Pharmaceutical compositions that include the disclosed compound may be prepared using methodology well known in the pharmaceutical art. A pharmaceutical composition that includes the disclosed compound may include a second effective compound of a distinct chemical formula from the disclosed compound. This second effective compound may have the same or a similar molecular target as the target or it may act upstream or downstream of the molecular target of the disclosed compound with regard to one or more biochemical pathways.

Pharmaceutical compositions including the disclosed compound include materials capable of modifying the physical form of a dosage unit. In one nonlimiting example, the composition includes a material that forms a coating that holds in the compound. Materials that may be used in such a coating, include, for example, sugar, shellac, gelatin, or any other inert coating agent. Pharmaceutical compositions including the disclosed compound may be prepared as a gas or aerosol. Aerosols encompass a variety of systems including colloids and pressurized packages. Delivery of a composition in this form may include propulsion of a pharmaceutical composition including the disclosed compound through use of liquefied gas or other compressed gas or by a suitable pump system. Aerosols may be delivered in single phase, bi-phasic, or tri-phasic systems.

In some aspects of the invention, the pharmaceutical composition including the disclosed compound is in the form of a solvate. Such solvates are produced by the dissolution of the disclosed compound in a pharmaceutically acceptable solvent. Pharmaceutically acceptable solvents include any mixtures of more than one solvent. Such solvents may include pyridine, chloroform, propan-1-ol, ethyl oleate, ethyl lactate, ethylene oxide, water, ethanol, and any other solvent that delivers a sufficient quantity of the disclosed compound to treat the affliction without serious complications arising from the use of the solvent in patients.

Pharmaceutical compositions that include the disclosed compound may also include a pharmaceutically acceptable carrier. Carriers include any substance that may be administered with the disclosed compound with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, oils (including petroleum, animal, vegetable or synthetic oils,) Such carriers include particulates such as a tablet or powder, liquids such as an oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or diglycerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition including the disclosed compound may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in "Remington's Pharmaceutical Sciences" by E. W. Martin, hereby incorporated by reference in its entirety.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intranasal, intracerebral, intraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery; topical application, by local injection; by a catheter; by a suppository; or by an implant. Administration may be by direct injection at the site (or former site) of a cancer, tumor, or precancerous tissue or into the central nervous system by any suitable route, including intraventricular and intrathecal injection. Intraventricular injection may be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. The disclosed compound may be delivered in the context of a vesicle such as a liposome or any other natural or synthetic vesicle.

A pharmaceutical composition formulated so as to be administered by injection may be prepared by dissolving the disclosed compound with water so as to form a solution. In addition, a surfactant may be added to facilitate the formation of a homogeneous solution or suspension. Surfactants include any complex capable of non-covalent interaction with the disclosed compound so as to facilitate dissolution or homogeneous suspension of the compound.

Pharmaceutical compositions including the disclosed compound may be prepared in a form that facilitates topical or transdermal administration. Such preparations may be in the form of a solution, emulsion, ointment, gel base, transdermal patch or iontophoresis device. Examples of bases used in such compositions include opetrolatum, lanolin, polyethylene glycols, beeswax, mineral oil, diluents such as water and alcohol, and emulsifiers and stabilizers, thickening agents, or any other suitable base now known or yet to be disclosed.

Examples that represent different aspects of the invention follow. Such examples should not be construed as limiting the scope of the disclosure. Alternative mechanistic pathways and analogous structures within the scope of the invention would be apparent to those skilled in the art.

Elements and acts in the examples are intended to illustrate the invention for the sake of simplicity and have not necessarily been rendered according to any particular sequence or embodiment.

EXAMPLES

Example 1. Synthesis of Kinase Inhibitors

Different aspects of the invention may be prepared via the general synthetic procedures outlined below. It will be apparent to one skilled in the art how to prepare the other aspects of the invention by choice of proper and relevant starting materials, synthetic intermediates and reagents.

A compound of Formula I can be prepared according to Scheme 1. A 1-[bis(dimethylamino)methylene]-1H-1,2,3-triazolo[4,5-b]pyridinium 3-oxid hexafluorophosphate (HATU) mediated amide coupling reaction between carboxylic acid 1 and amine 2 in DMF (N,N-dimethylformamide) generates structure 3. Under the same conditions, amine 4 reacts with 5 to generate structure 6.

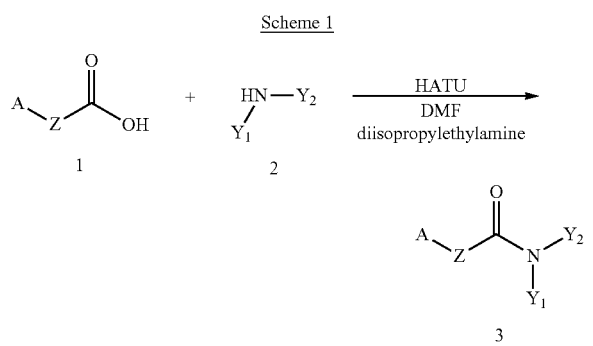

Another compound of Formula I can be prepared according to Scheme 2. The coupling of amine 4 and phenyl chloroformate yields structure 7, which is treated with amine 2 to afford urea 9.

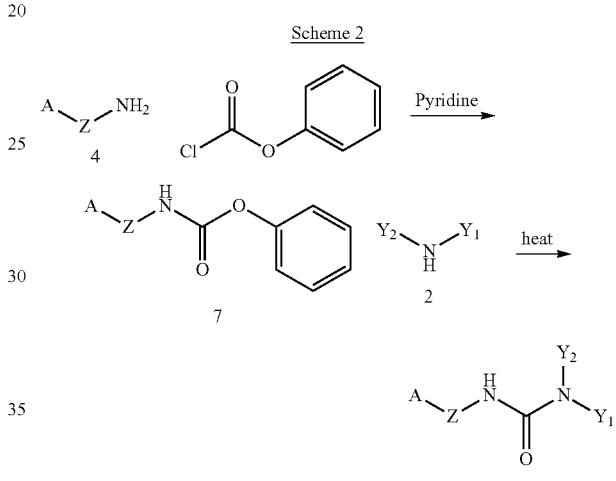

A compound of Formula V can be prepared according to Scheme 3. Aniline diamine 10 and isothiocyanate 11 are heated in THF and the cyclization of the resulting thiourea with iodomethane yields aminoimidazole 12.

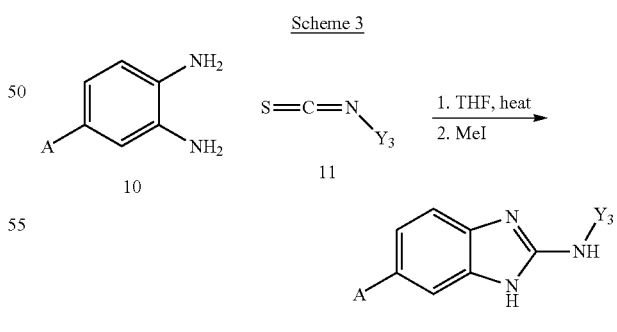

Example 2. Kinase Inhibitor Compounds

Non-limiting examples illustrative of the invention include those shown in Table 1.

TABLE 1

Non-limiting examples of kinase inhibitor compounds. Unless specified, example compounds with a chiral center represent racemic mixture of the corresponding R and S enantiomers and all racemates and isolated enantiomers are within the scope of the invention.

| ID | Structure | M + 1 |
| --- | --- | --- |
| 1 | 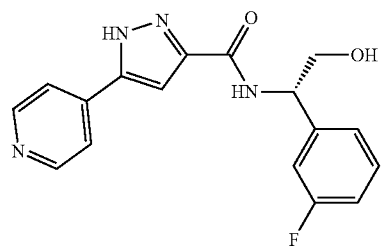 | 327 |
| 2 | 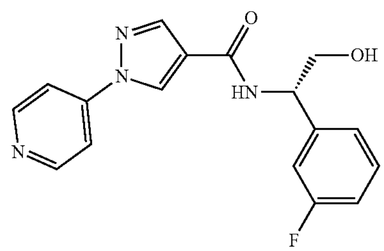 [SMILES: O=C(N[C@H](CO)c1cccc(F)c1)c1cnn(-c2ccncc2)c1] | 327 |
| 3 | 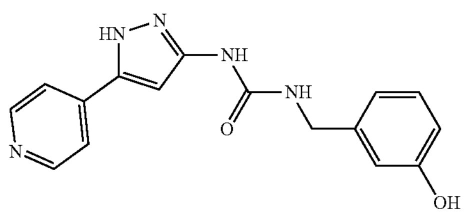 [SMILES: O=C(NCc1cccc(O)c1)Nc1cc(-c2ccncc2)[nH]n1] | 310 |
| 4 | 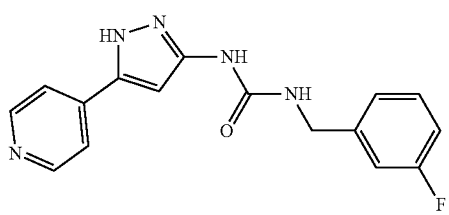 [SMILES: O=C(NCc1cccc(F)c1)Nc1cc(-c2ccncc2)[nH]n1] | 312 |
| 5 | 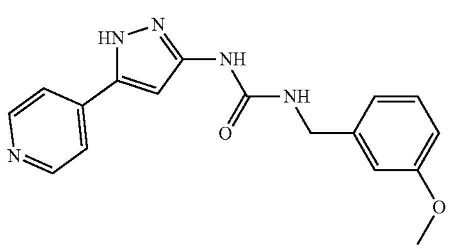 [SMILES: COc1cccc(CNC(=O)Nc2cc(-c3ccncc3)[nH]n2)c1] | 324 |
| 6 | 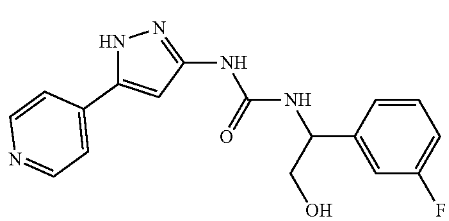 [SMILES: O=C(Nc1cc(-c2ccncc2)[nH]n1)NC(CO)c1cccc(F)c1] | 342 |

TABLE 1-continued

Non-limiting examples of kinase inhibitor compounds. Unless specified, example compounds with a chiral center represent racemic mixture of the corresponding R and S enantiomers and all racemates and isolated enantiomers are within the scope of the invention.

| ID | Structure | M + 1 |
|---|---|---|
| 7 | 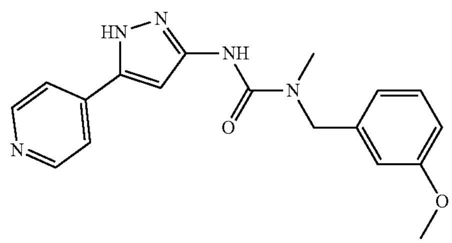 [SMILES: COc1cccc(CN(C)C(=O)Nc2cc(-c3ccncc3)[nH]n2)c1] | 338 |
| 8 | 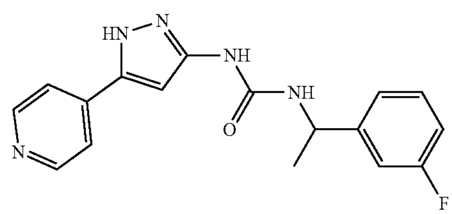 [SMILES: CC(NC(=O)Nc1cc(-c2ccncc2)[nH]n1)c1cccc(F)c1] | 326 |
| 9 | 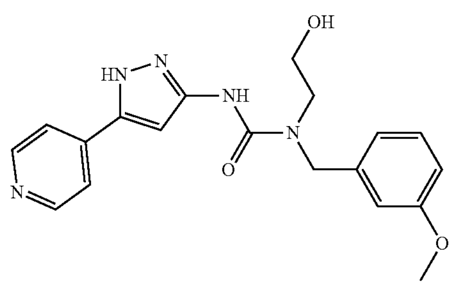 [SMILES: COc1cccc(CN(CCO)C(=O)Nc2cc(-c3ccncc3)[nH]n2)c1] | 368 |
| 10 | 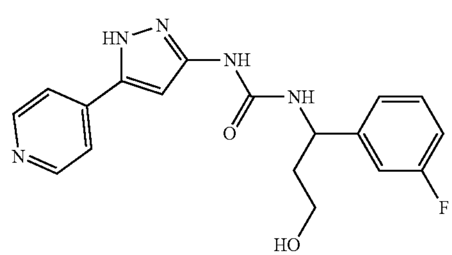 [SMILES: O=C(Nc1cc(-c2ccncc2)[nH]n1)NC(CCO)c1cccc(F)c1] | 356 |
| 11 | 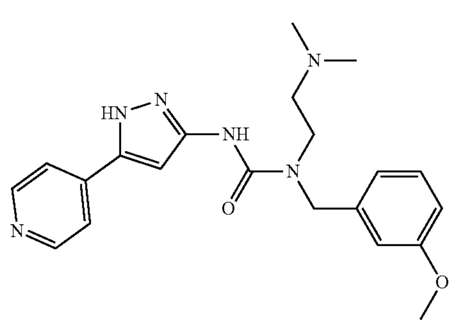 [SMILES: COc1cccc(CN(CCN(C)C)C(=O)Nc2cc(-c3ccncc3)[nH]n2)c1] | 395 |

TABLE 1-continued

Non-limiting examples of kinase inhibitor compounds. Unless specified, example compounds with a chiral center represent racemic mixture of the corresponding R and S enantiomers and all racemates and isolated enantiomers are within the scope of the invention.

| ID | Structure | M + 1 |
|---|---|---|
| 12 | 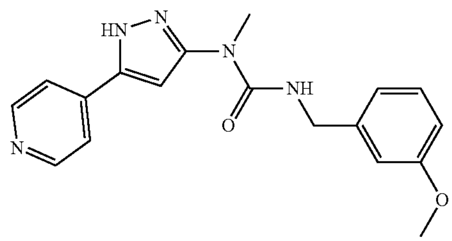 [SMILES: COc1cccc(CNC(=O)N(C)c2cc(-c3ccncc3)[nH]n2)c1] | 338 |
| 13 | 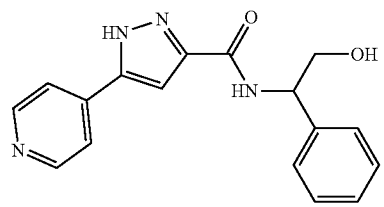 [SMILES: O=C(NC(CO)c1ccccc1)c1cc(-c2ccncc2)[nH]n1] | 309 |
| 14 | 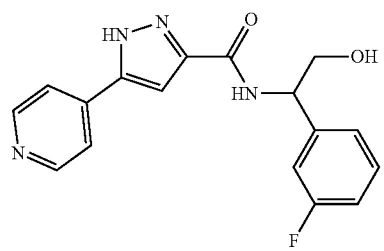 [SMILES: O=C(NC(CO)c1cccc(F)c1)c1cc(-c2ccncc2)[nH]n1] | 327 |
| 15 | 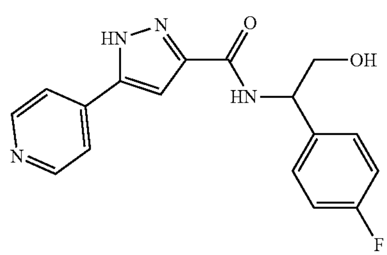 [SMILES: O=C(NC(CO)c1ccc(F)cc1)c1cc(-c2ccncc2)[nH]n1] | 327 |
| 16 | 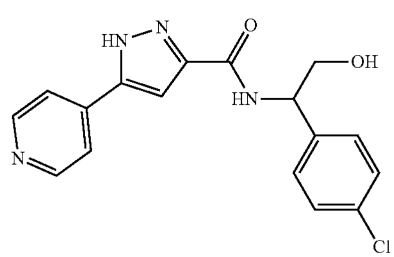 [SMILES: O=C(NC(CO)c1ccc(Cl)cc1)c1cc(-c2ccncc2)[nH]n1] | 343 |
| 17 | 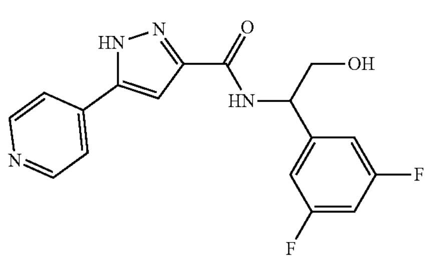 [SMILES: O=C(NC(CO)c1cc(F)cc(F)c1)c1cc(-c2ccncc2)[nH]n1] | 345 |

TABLE 1-continued
Non-limiting examples of kinase inhibitor compounds. Unless specified, example compounds with a chiral center represent racemic mixture of the corresponding R and S enantiomers and all racemates and isolated enantiomers are within the scope of the invention.
| ID | Structure | M + 1 |
|---|---|---|
| 18 | 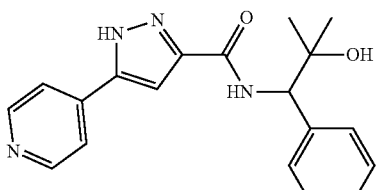 | 337 |
| 19 | 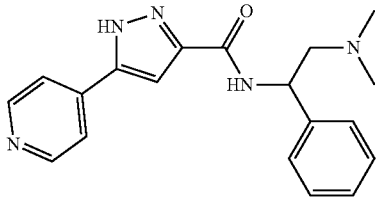 [SMILES: CN(C)CC(NC(=O)c1cc(-c2ccncc2)[nH]n1)c1ccccc1] | 336 |
| 20 | 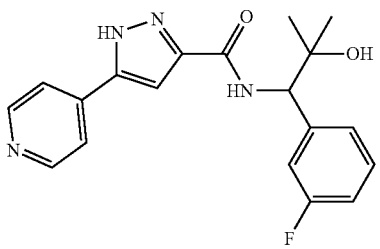 [SMILES: CC(C)(O)C(NC(=O)c1cc(-c2ccncc2)[nH]n1)c1cccc(F)c1] | 355 |
| 21 | 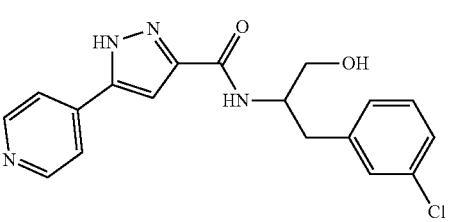 [SMILES: O=C(NC(CO)Cc1cccc(Cl)c1)c1cc(-c2ccncc2)[nH]n1] | 357 |
| 22 | 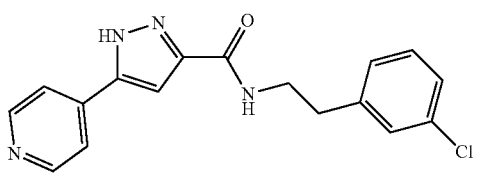 [SMILES: O=C(NCCc1cccc(Cl)c1)c1cc(-c2ccncc2)[nH]n1] | 327 |
| 23 | 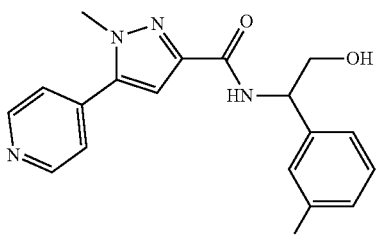 | 341 |

TABLE 1-continued

Non-limiting examples of kinase inhibitor compounds. Unless specified, example compounds with a chiral center represent racemic mixture of the corresponding R and S enantiomers and all racemates and isolated enantiomers are within the scope of the invention.

| ID | Structure | M + 1 |
|----|-----------|-------|
| 24 | 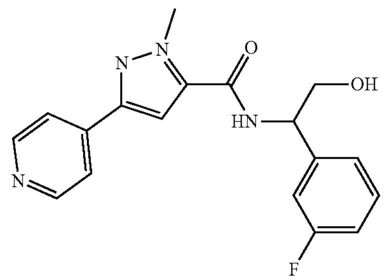 | 341 |
| 25 | 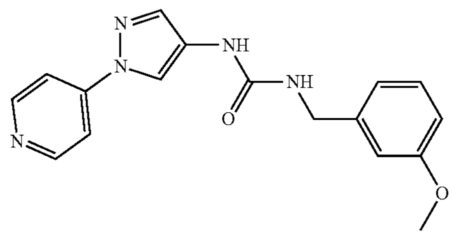 | 324 |
| 26 | 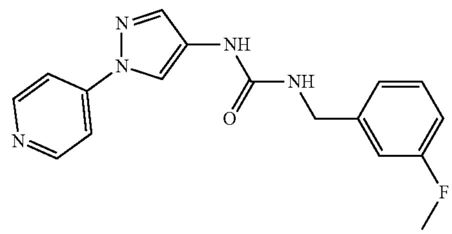 [SMILES: COc1cccc(CNC(=O)Nc2cnn(-c3ccncc3)c2)c1] | 312 |
| 27 | 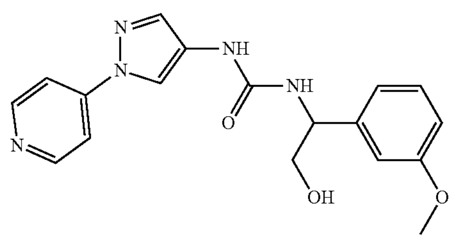 [SMILES: COc1cccc(C(CO)NC(=O)Nc2cnn(-c3ccncc3)c2)c1] | 354 |
| 28 | 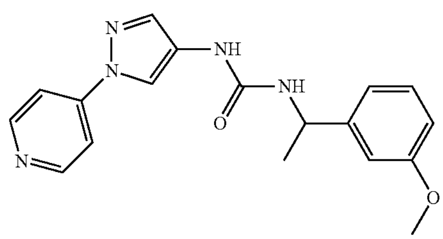 [SMILES: COc1cccc(C(C)NC(=O)Nc2cnn(-c3ccncc3)c2)c1] | 338 |
| 29 | 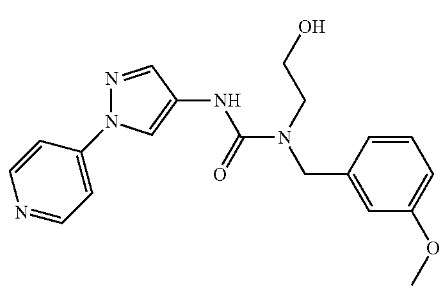 [SMILES: COc1cccc(CN(CCO)C(=O)Nc2cnn(-c3ccncc3)c2)c1] | 368 |

TABLE 1-continued

Non-limiting examples of kinase inhibitor compounds. Unless specified, example compounds with a chiral center represent racemic mixture of the corresponding R and S enantiomers and all racemates and isolated enantiomers are within the scope of the invention.

| ID | Structure | M + 1 |
|---|---|---|
| 30 | 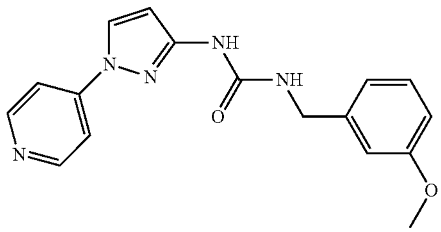 [SMILES: COc1cccc(CNC(=O)Nc2ccn(-c3ccncc3)n2)c1] | 324 |
| 31 | 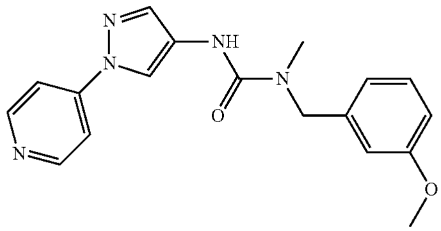 [SMILES: COc1cccc(CN(C)C(=O)Nc2cnn(-c3ccncc3)c2)c1] | 338 |
| 32 | 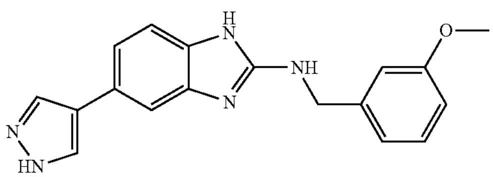 [SMILES: COc1cccc(CNc2nc3cc(-c4cn[nH]c4)ccc3[nH]2)c1] | 320 |
| 33 | 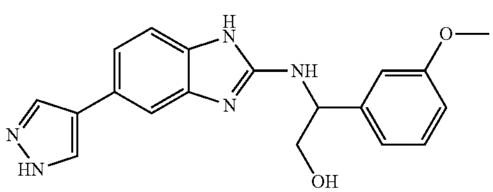 [SMILES: COc1cccc(C(CO)Nc2nc3cc(-c4cn[nH]c4)ccc3[nH]2)c1] | 350 |
| 34 | 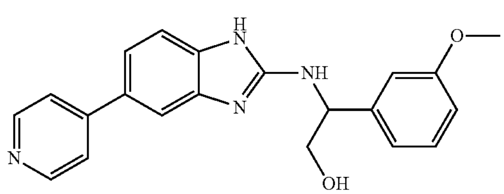 [SMILES: COc1cccc(C(CO)Nc2nc3cc(-c4ccncc4)ccc3[nH]2)c1] | 361 |
| 35 | 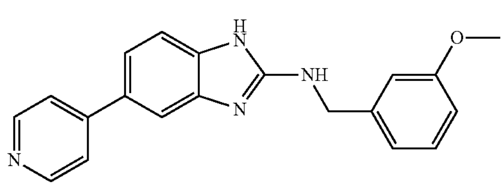 [SMILES: COc1cccc(CNc2nc3cc(-c4ccncc4)ccc3[nH]2)c1] | 331 |
| 36 | 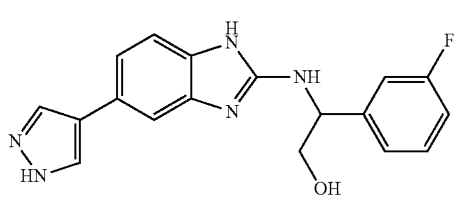 [SMILES: OCC(Nc1nc2cc(-c3cn[nH]c3)ccc2[nH]1)c1cccc(F)c1] | 338 |

TABLE 1-continued

*Non-limiting examples of kinase inhibitor compounds. Unless specified, example compounds with a chiral center represent racemic mixture of the corresponding R and S enantiomers and all racemates and isolated enantiomers are within the scope of the invention.*

| ID | Structure | M + 1 |
|----|-----------|-------|
| 37 | 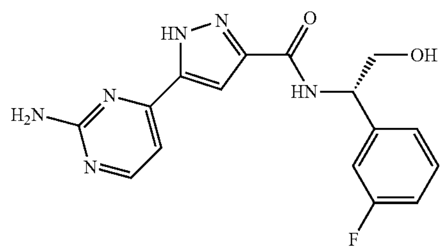 [SMILES: Nc1nccc(-c2cc(C(=O)N[C@H](CO)c3cccc(F)c3)n[nH]2)n1] | 343 |
| 38 | 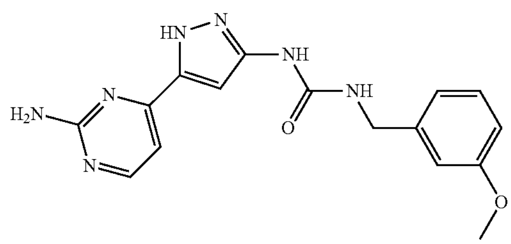 [SMILES: COc1cccc(CNC(=O)Nc2cc(-c3ccnc(N)n3)[nH]n2)c1] | 340 |
| 39 | 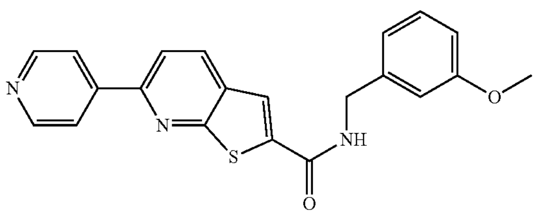 [SMILES: COc1cccc(CNC(=O)c2cc3ccc(-c4ccncc4)nc3s2)c1] | 376 |
| 40 | 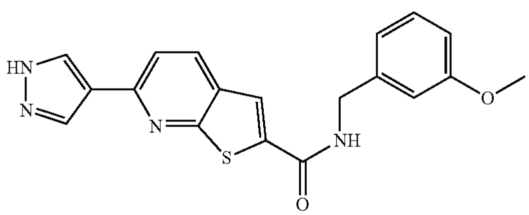 [SMILES: COc1cccc(CNC(=O)c2cc3ccc(-c4cn[nH]c4)nc3s2)c1] | 365 |
| 41 | 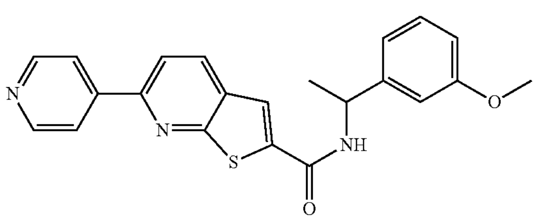 | 390 |
| 42 | 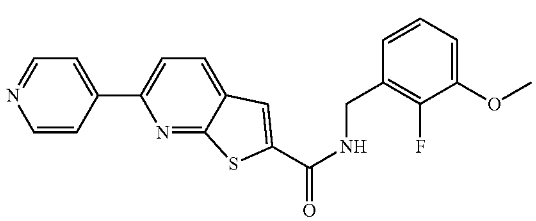 [SMILES: COc1cccc(CNC(=O)c2cc3ccc(-c4ccncc4)nc3s2)c1F] | 394 |

TABLE 1-continued

Non-limiting examples of kinase inhibitor compounds. Unless specified, example compounds with a chiral center represent racemic mixture of the corresponding R and S enantiomers and all racemates and isolated enantiomers are within the scope of the invention.

| ID | Structure | M + 1 |
|----|-----------|-------|
| 43 | 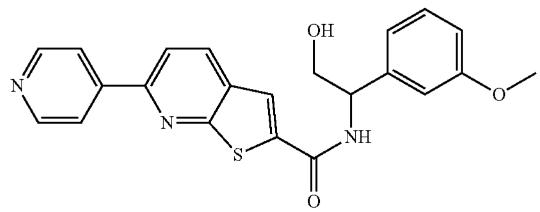 [SMILES: COc1cccc(C(CO)NC(=O)c2cc3ccc(-c4ccncc4)nc3s2)c1] | 406 |
| 44 | 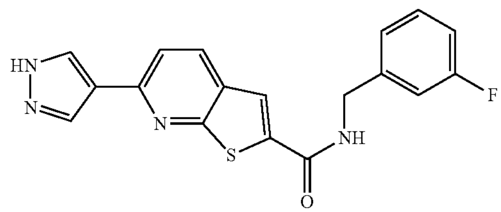 [SMILES: O=C(NCc1cccc(F)c1)c1cc2ccc(-c3cn[nH]c3)nc2s1] | 353 |
| 45 | 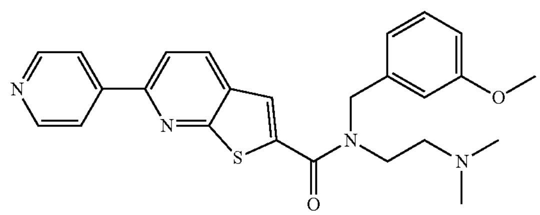 [SMILES: COc1cccc(CN(CCN(C)C)C(=O)c2cc3ccc(-c4ccncc4)nc3s2)c1] | 447 |
| 46 | 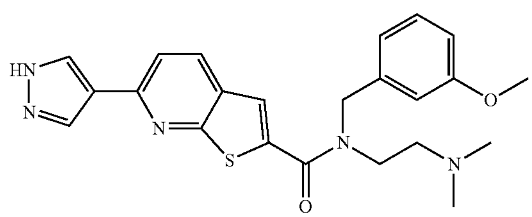 [SMILES: COc1cccc(CN(CCN(C)C)C(=O)c2cc3ccc(-c4cn[nH]c4)nc3s2)c1] | 436 |
| 47 | 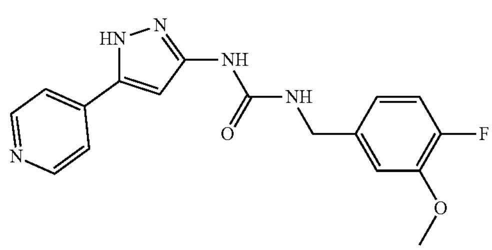 [SMILES: COc1cc(CNC(=O)Nc2cc(-c3ccncc3)[nH]n2)ccc1F] | 342 |
| 48 | 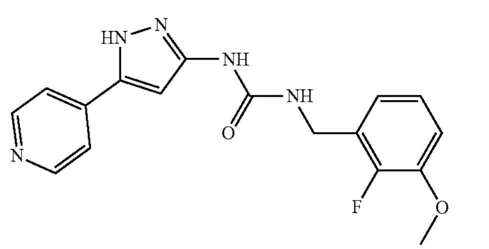 [SMILES: COc1cccc(CNC(=O)Nc2cc(-c3ccncc3)[nH]n2)c1F] | 342 |

TABLE 1-continued

Non-limiting examples of kinase inhibitor compounds. Unless specified, example compounds with a chiral center represent racemic mixture of the corresponding R and S enantiomers and all racemates and isolated enantiomers are within the scope of the invention.

| ID | Structure | M + 1 |
|----|-----------|-------|
| 49 | 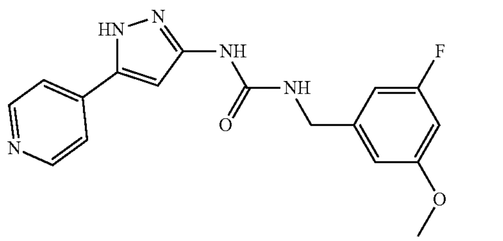 [SMILES: COc1cc(F)cc(CNC(=O)Nc2cc(-c3ccncc3)[nH]n2)c1] | 342 |
| 50 | 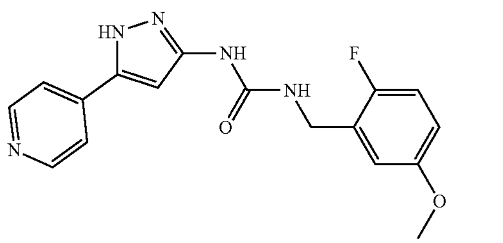 [SMILES: COc1ccc(F)c(CNC(=O)Nc2cc(-c3ccncc3)[nH]n2)c1] | 342 |
| 51 | 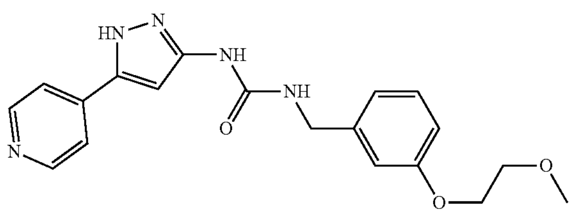 [SMILES: COCCOc1cccc(CNC(=O)Nc2cc(-c3ccncc3)[nH]n2)c1] | 368 |
| 52 | 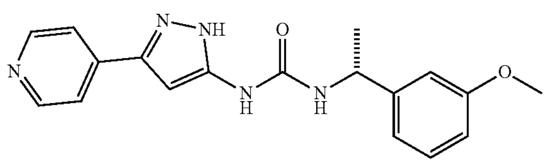 [SMILES: COc1cccc([C@@H](C)NC(=O)Nc2cc(-c3ccncc3)n[nH]2)c1] | 338 |
| 53 | 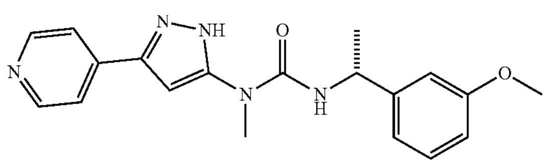 [SMILES: COc1cccc([C@@H](C)NC(=O)N(C)c2cc(-c3ccncc3)n[nH]2)c1] | 352 |
| 54 | 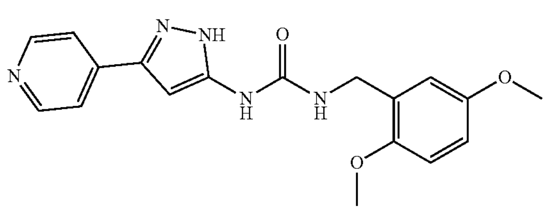 [SMILES: COc1ccc(OC)c(CNC(=O)Nc2cc(-c3ccncc3)n[nH]2)c1] | 354 |
| 55 | 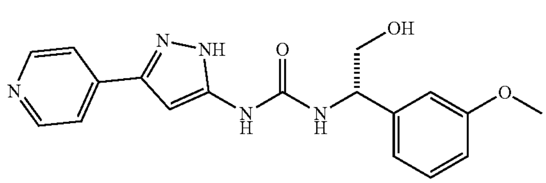 [SMILES: COc1cccc([C@@H](CO)NC(=O)Nc2cc(-c3ccncc3)n[nH]2)c1] | 354 |

TABLE 1-continued

Non-limiting examples of kinase inhibitor compounds. Unless specified, example compounds with a chiral center represent racemic mixture of the corresponding R and S enantiomers and all racemates and isolated enantiomers are within the scope of the invention.

| ID | Structure | M + 1 |
|---|---|---|
| 56 | 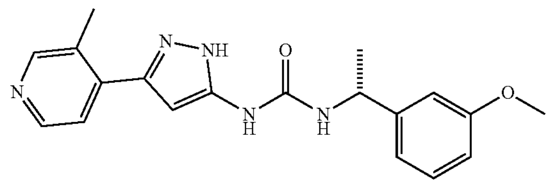 [SMILES: COc1cccc([C@@H](C)NC(=O)Nc2cc(-c3ccncc3C)n[nH]2)c1] | 352 |
| 57 | 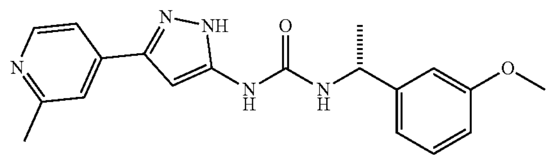 [SMILES: COc1cccc([C@@H](C)NC(=O)Nc2cc(-c3ccnc(C)c3)n[nH]2)c1] | 352 |

Example 3. Synthesis of Compound 14

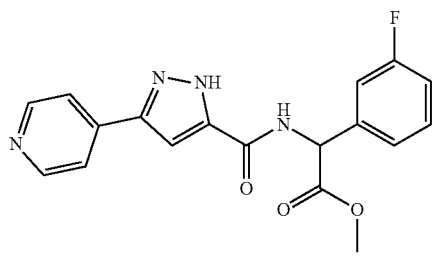 [SMILES: COC(=O)C(NC(=O)c1cc(-c2ccncc2)n[nH]1)c1cccc(F)c1]

methyl 2-(3-fluorophenyl)-2-(3-(pyridin-4-yl)-1H-pyrazole-5-carboxamido)acetate

To a mixture of 3-(pyridin-4-yl)-1H-pyrazole-5-carboxylic acid (95 mg, 0.50 mmol), methyl 2-amino-2-(3-fluorophenyl)acetate HCl salt (143 mg, 0.65 mmol) and diisopropylethylamine (0.26 mL, 1.5 mmol) in DMF was added HATU (248 mg, 0.65 mmol). The reaction was stirred at room temperature for 3 h, quenched with water and extracted with ethyl acetate. The organic layer was dried, concentrated and purified by BIOTAGE® column chromatography to give methyl 2-(3-fluorophenyl)-2-(3-(pyridin-4-yl)-1H-pyrazole-5-carboxamido)acetate (126 mg).

Step 2

Compound 14

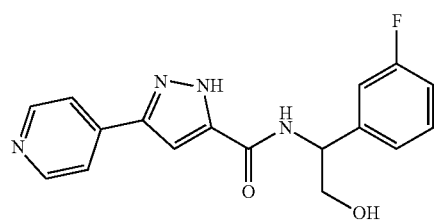

To a solution of methyl 2-(3-fluorophenyl)-2-(3-(pyridin-4-yl)-1H-pyrazole-5-carboxamido) acetate (62 mg, 0.17 mmol) in MeOH was added sodium borohydride (13 mg, 0.34 mmol). The reaction was stirred overnight, quenched with NaOH (1N) and concentrated. The residue was purified by C-18 BIOTAGE® column chromatography to give Compound 14 (29 mg).

Example 4. Synthesis of Compound 39

Step 1

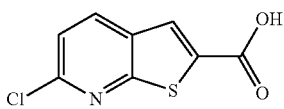

6-chlorothieno[2,3-b]pyridine-2-carboxylic acid

To a suspension of 2-bromo-6-chlorothieno[2,3-b]pyridine (100 mg, 0.40 mmol) in ether was added n-butyllithium (0.29 mL, 2.5 M, 0.72 mmol) dropwise at −40° C. The reaction was stirred for 0.5 h, quenched with excess dry ice and partitioned between water and ethyl acetate. The organic layer was dried, concentrated and purified by C-18 BIOTAGE® column chromatography to give 6-chlorothieno[2,3-b]pyridine-2-carboxylic acid (36 mg).

Step 2

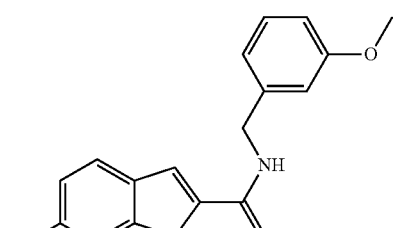

6-chloro-N-(3-methoxybenzyl)thieno[2,3-b]pyridine-2-carboxamide 6-chloro-N-(3-methoxybenzyl)thieno[2,3-b]pyridine-2-carboxamide was prepared from 6-chlorothieno[2,3-b]pyridine-2-carboxylic acid by following the synthesis method of Step 2 in Example 3.

Step 3

Compound 39

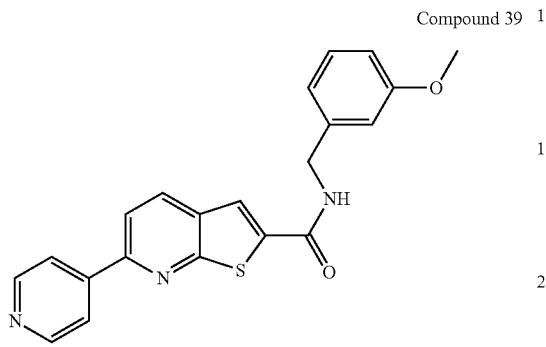

A mixture of 6-chloro-N-(3-methoxybenzyl)thieno[2,3-b]pyridine-2-carboxamide (25 mg, 0.075 mmol), pyridine-4-boronic acid (30 mg, 0.22 mmol), [1,1'-Bis(diphenylphosphino)ferrocene]dichloropalladium(II) (5 mg, 5%) and cesium carbonate (95 mg, 0.3 mmol) in 1,4-dioxane was heated to 100° C. and stirred under nitrogen atmosphere overnight. The mixture was filtered through a Celite pad. The filtrate was concentrated and purified by BIOTAGE® C-18 column chromatography to give Compound 39 (12 mg).

Example 5. ROCK1 and ROCK2 Kinase Inhibition Assays

The following assay protocol is for measuring the phosphorylation of a peptide substrate (FAM-KKLRRTLSVA-OH wherein FAM is carboxyfluorescein). The peptide is >98% purity by Capillary Electrophoresis. The peptide is phosphorylated by the protein kinase ROCK1 or ROCK2. The ROCK1 or ROCK2 enzyme, substrate, and cofactors (ATP and $Mg^{2+}$) are combined in a well of a microtiter plate and incubated for 3 hours at 25° C. At the end of the incubation, the reaction is quenched by the addition of an EDTA-containing buffer. The substrate and product are separated and quantified electrophoretically using the microfluidic-based LABCHIP® 3000 Drug Discovery System from Caliper Life Sciences (Hopkinton, Mass.).

The components of the assay mixture are:
100 mM HEPES, pH 7.5
0.1% BSA
0.01% Triton X-100
1 mM DTT
10 mM $MgCl_2$
10 μM Sodium Orthovanadate
10 μM Beta-Glycerophosphate
5 μM ATP (for ROCK1) or 7 μM ATP (for ROCK2)
1% DMSO (from compound)
1.25 μM FAM-KKLRRTLSVA-OH
3 nM ROCK1 or 2.5 nM ROCK2 enzyme Substrate and product peptides present in each sample are separated electrophoretically using the LABCHIP® 3000 capillary electrophoresis instrument. As substrate and product peptides are separated two peaks of fluorescence are observed. Change in the relative fluorescence intensity of the substrate and product peaks is the parameter measured reflecting enzyme activity. Capillary electrophoregramms (RDA acquisition files) are analyzed using HTS Well Analyzer software (Caliper Life Sciences, Hopkinton, Mass.). The kinase activity in each sample is determined as the product to sum ratio (PSR): P/(S+P), where P is the peak height of the product peptide and S is the peak height of the substrate peptide. For each compound, enzyme activity is measured at various concentrations (12 concentrations of compound spaced by 3× dilution intervals). Negative control samples (0%–inhibition in the absence of inhibitor) and positive control samples (100%–inhibition in the presence of 20 mM EDTA) are assembled in replicates of four and are used to calculate %-inhibition values for each compound at each concentration. Percent inhibition (Pinh) is determined using the following equation:

Pin$h$=(PSR0%−PSRin$h$)/(PSR0%−PSR100%)*100 where PSRinh is the product sum ratio in the presence of inhibitor, PSR0% is the average product sum ratio in the absence of inhibitor, and PSR100% is the average product sum ratio in 100%-inhibition control samples. The $IC_{50}$ values of inhibitors are determined by fitting the inhibition curves (Pinh versus inhibitor concentration) by 4 parameter sigmoidal dose-response model using XLfit 4 software (IBDS).

This assay can be used to test the activity of each of the exemplary compounds identified in Table 1. It is expected that each of these compounds will demonstrate inhibition of the protein kinase ROCK1 and/or ROCK2.

Example 6. Cell Viability Assay

Cell viability in the presence of varying concentrations of the above listed compounds at different time points was used to assess cytotoxicity and the effect of the compounds on cell proliferation. $IC_{50}$ (or percent activity) data for the compounds of the present invention in K562 or MV411 cell lines are summarized in Table 2.

Cell Viability Assay—

Cell viability was measured by the CELLTITER-GlO cell viability assay from Promega (Madison, Wis.). The CELLTITER-GlO Luminescent Cell Viability Assay is a homogeneous method to determine the number of viable cells in culture based on quantitation of the ATP present, which signals the presence of metabolically active cells. Following treatment, CELLTITER-GlO is added to treatment wells and incubated at 37° C. luminescence values were measured at using a Molecular Devices Spectramax microplate reader.

Experimental Design

Single Agent Studies—

Cells were grown to 70% confluency, trypsinized, counted, and seeded in 96 well flat-bottom plates at a final concentration of $2.5 \times 10^3$-$5 \times 10^3$ cells/well (Day 0). Cells were allowed to incubate in growth media for 24 hours. Treatment with the test agents or standard agents began on Day 1 and continued for 72 hours. At the 72-hour time point, treatment containing media was removed. Viable cell numbers were quantified by the CELLTITER-GLO® cell viability assay as described above. Results from these studies were used to calculate an $IC_{50}$ value (concentration of drug that inhibits cell growth by 50 percent of control) for each compound.

Data Collection—

For single agent and combination studies, data from each experiment was collected and expressed as % Cell Growth using the following calculation:

% Cell Growth=$(f_{test}/f_{vehicle})\times 100$

Where $f_{test}$ is the luminescence of the tested sample, and $f_{vehicle}$ is the luminescence of the vehicle in which the drug is dissolved. Dose response graphs and $IC_{50}$ values were generated using Prism 6 software (GraphPad) using the following equation:

$Y=(Top-Bottom)/(1+10^{((\log IC50-X)-HillSlope)})$

Where X is the logarithm of the concentration and Y is the response. Y starts at the Bottom and goes to the Top with a sigmoid shape.

Example 7. ROCK1 and ROCK2 Kinase Inhibition and Cell Viability Assay Results The protocols outlined in Examples 5 and 6 were followed to test ROCK1 and ROCK2 kinase inhibition and cancer cell viability with compounds from Table 1. As shown in Table 2, the compounds demonstrated inhibition of the ROCK1 and ROCK2 kinases and growth of cancer cells.

The experiments also evaluated the selectivity of the compounds for inhibiting growth of cancer cells carrying a mutation in the Flt3 gene. The MV411 cell line expresses the mutant allele of Flt3 with internal tandem duplications (ITD) of the gene. See Quentmeier et al., "FLT3 Mutations in Acute Myeloid Leukemia Cell Lines," Leukemia 17(1), 2003, 120-124. K562 is a chronic myeloid leukemia cell line that does not express FLT3 protein. See Grafone et al., "Monitoring of FLT3 Phosphorylation Status and Its Response to Drugs By Flow Cytometry in AML Blast Cells," Hematol Oncol. 26(3), 2008, 159-166. Patients with ITD-FLT3[+] acute myeloid leukemia (AML) experience an extremely poor prognosis. Surprisingly, many of the compounds demonstrated greater efficacy with the MV11 cells than with the K562 cells suggesting that these compounds could be used to effectively treat ITD-FLT3[+] AML.

TABLE 2

ROCK1 and ROCK2 kinase inhibition and cell viability

| Compound ID | ROCK1 IC$_{50}$ (nM) | ROCK2 IC$_{50}$ (nM) | K562* (μM) | MV411* (μM) | FLT3-ITD[+] Selectivity (K562/MV411) |
|---|---|---|---|---|---|
| 1 | 207 | 98 | >100 | 67.6 | >1 |
| 3 |  | >100 |  | 43.7 | >2 |
| 5 | 73 | 16.1 | 43.6 | 10.2 | 4 |
| 7 | 102 | 22.9 | 89.1 | 7.6 | 12 |
| 9 | 237 | 39.1 | 97.2 | 39.8 | 2 |
| 11 | 63.6 | 22.1 | >100 | 14.5 | >7 |
| 25 | 130 | 28.7 | 85 | 34 | 3 |
| 40 | 65.1 | 17.4 | >100 | 7.1 | >14 |
| 47 |  |  | 17.8 | 7.8 | 2 |
| 48 | 6400 | 1870 |  |  |  |
| 49 |  |  | 17.8 | 7.8 | 2 |
| 50 | 1010 | 239 | >100 | 7.8 | >13 |
| 51 |  |  | >100 | 17.0 | >6 |
| 52 | 34 | 8.7 | >100 | 11.2 | >9 |
| 53 |  |  | 64.6 | 93.3 | 1 |
| 54 |  |  | >100 | 12.6 | >8 |
| Compound A** | 3.3 | 2.8 | 0.8 | 0.7 | 1 |

*MV411 is ITD-FLT3[+], and K562 does not express ITD-FLT3. Rho-associated kinase may be manipulated for the treatment of ITD-FLT3[+] AML as reported in Onish et at., "Internal Tandem Duplication Mutations in FLT3 Gene Augment Chemotaxis to Cxcl12 Protein by Blocking the Down-regulation of the Rho-associated Kinase via the Cxcl12/Cxcr4 Signaling Axis," J. Biol. Chem. 289 (45), 2014, 31053-31065.

**Compound A is shown below and is described by Schirok et al., "Design and Synthesis of Potent and Selective Azaindole-Based Rho Kinase (ROCK) Inhibitors," ChemMedChem 3, 2008, 1893-1904.

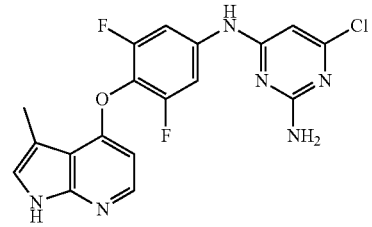

Compound A

Unless defined otherwise, all technical and scientific terms herein have the same meaning as commonly understood by one of ordinary skill in the art to which this invention belongs. All publications, patents, and patent publications cited are incorporated by reference herein in their entirety for all purposes.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A compound of Formula (I):

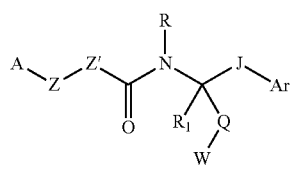

or an enantiomer, a mixture of enantiomers, or a mixture of two or more diastereomers thereof; or a pharmaceutically acceptable salt, solvate, or hydrate thereof;

wherein:

A is indazol-3-yl, pyrazol-4-yl, or

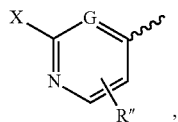

wherein
(i) G is CR' or N;
(ii) X is hydrogen, $C_{1-6}$ alkyl, $C_{3-7}$ cycloalkyl, —$OR_2$ or —$NR_3R_4$; and
(iii) R', R", $R_2$, $R_3$ and $R_4$ are independently —H, $C_{1-6}$ alkyl or $C_{3-7}$ cycloalkyl;

Z is

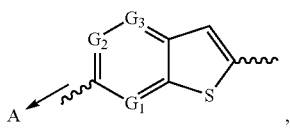

wherein
$G_1$, $G_2$ and $G_3$ are independently CH or N;
Z' is a bond;
R is —H, $C_{1-6}$ alkyl or $C_{3-7}$ cycloalkyl;
$R_1$ is —H;
Q is a bond or methyl;
J is a bond;
W is —H or —OH; and
Ar is a phenyl, naphthyl, or C5-10 heterocycle, each of which is substituted with halo, —OH, —CN, —$COOR_a$, —$OR_a$, —$SR_a$, —$OC(O)R_a$, —$NHR_a$, —$NR_aR_b$, —$NHC(O)R_a$, —$NHC(O)NR_aR_b$, —$C(O)NR_aR_b$, —$NS(O)_2R_a$, —$S(O)_2NR_aR_b$, —$S(O)_2R_a$, guanidino, nitro, nitroso, $C_{1-6}$ alkyl, aryl, $C_{3-7}$ cycloalkyl, or 3- to 10-membered heterocycle, wherein the $C_{1-6}$ alkyl, aryl, $C_{3-7}$ cycloalkyl, or 3 to 10-membered heterocycle is unsubstituted or substituted with one or more of halo, —OH, —CN, —$COOR_a$, —$OR_a$, —$SR_a$, —$OC(O)R_a$, —$NHR_a$, —$NR_aR_b$, —$NHC(O)R_a$, —$NHC(O)NR_aR_b$, —$C(O)NR_aR_b$, —$NS(O)_2R_a$, —$S(O)_2NR_aR_b$, —$S(O)_2R_a$, guanidino, nitro, nitroso, $C_{1-6}$ alkyl, aryl, or $C_{3-7}$ cycloalkyl; wherein each of $R_a$ and $R_b$ is independently —H or $C_{1-6}$ alkyl; and optionally $R_a$ and $R_b$ together attaching to N or O form a 4- to 8-membered heterocycle.

2. The compound of claim 1, wherein A is pyrazol-4-yl.
3. The compound of claim 2, wherein $G_1$ is N; and $G_2$ and $G_3$ are CH.
4. The compound of claim 3, wherein Q is methyl.
5. The compound of claim 4, wherein Ar is a substituted phenyl.
6. The compound of claim 5, wherein the phenyl is substituted with —$OR_a$ and $R_a$ is —H or $C_{1-6}$ alkyl.
7. The compound of claim 5, wherein R is —H.
8. A method of treating a neoplastic disease in a subject comprising: administering to the subject a therapeutically effective amount of a compound of claim 1, wherein the neoplastic disease is a disorder associated with inappropriate ROCK activity.
9. The method of claim 8, wherein the neoplastic disorder is a lymphoma, carcinoma, leukemia, sarcoma, or blastoma.
10. The method of claim 9, wherein the neoplastic disorder is acute myeloid leukemia (AML).
11. The method of claim 10, wherein the AML is ITD-FLT3$^+$ AML.
12. The compound of claim 3, wherein Ar is a substituted phenyl.
13. The compound of claim 12, wherein the phenyl is substituted with —$OR_a$ and $R_a$ is —H or $C_{1-6}$ alkyl.
14. The compound of claim 13, wherein $R_a$ is methyl.
15. The compound of claim 14, wherein R is —H.
16. The compound of claim 2, wherein Ar is a substituted phenyl.
17. The compound of claim 16, wherein the phenyl is substituted with —$OR_a$ and $R_a$ is —H or $C_{1-6}$ alkyl.
18. The compound of claim 17, wherein $R_a$ is methyl.
19. The compound of claim 18, wherein R is —H.
20. The compound of claim 12, wherein Q is methyl and W is —H.
21. The compound of claim 20, wherein the configuration of the compound is R.
22. The compound of claim 12, wherein Q is methyl and W is —OH.
23. The compound of claim 22, wherein the configuration of the compound is S.
24. The compound of claim 6, wherein $R_a$ is methyl.

* * * * *